US010619206B2

(12) United States Patent
Amorese et al.

(10) Patent No.: US 10,619,206 B2
(45) Date of Patent: *Apr. 14, 2020

(54) SEQUENTIAL SEQUENCING

(71) Applicant: NuGen Technologies, Inc., San Carlos, CA (US)

(72) Inventors: Doug Amorese, Los Altos, CA (US); Benjamin G. Schroeder, San Mateo, CA (US); Jonathan Scolnick, San Francisco, CA (US)

(73) Assignee: Tecan Genomics, Redwood City, CA (US)

( * ) Notice: Subject to any disclaimer, the term of this patent is extended or adjusted under 35 U.S.C. 154(b) by 139 days.

This patent is subject to a terminal disclaimer.

(21) Appl. No.: 15/809,638

(22) Filed: Nov. 10, 2017

(65) Prior Publication Data

US 2018/0112264 A1 Apr. 26, 2018

Related U.S. Application Data

(63) Continuation of application No. 14/778,564, filed as application No. PCT/US2014/028356 on Mar. 14, 2014, now Pat. No. 9,822,408.
(Continued)

(51) Int. Cl.
*C12Q 1/6874* (2018.01)
*G16B 30/00* (2019.01)

(52) U.S. Cl.
CPC .......... *C12Q 1/6874* (2013.01); *G16B 30/00* (2019.02)

(58) Field of Classification Search
CPC ................................................. C12Q 1/6874
See application file for complete search history.

(56) References Cited

U.S. PATENT DOCUMENTS 4,362,867 A 12/1982 Paddock
4,458,066 A 7/1984 Caruthers et al.
(Continued)

FOREIGN PATENT DOCUMENTS

CA 2444926 A1 11/2002
CN 1661102 A 8/2005
(Continued)

OTHER PUBLICATIONS

Merriman, B. et al., Progress in Ion Torrent semiconductor chip based sequencing, Electrophoresis, vol. 35, pp. 3397-3417 (Year: 2012).*
(Continued)

*Primary Examiner* — Teresa E Strzelecka
(74) *Attorney, Agent, or Firm* — Brown Rudnick LLP; Thomas C. Meyers

(57) ABSTRACT

Described herein are improved methods, compositions and kits for next generation sequencing (NGS). The methods, compositions and kits described herein enable phasing of two or more nucleic acid sequences in a sample, i.e. determining whether the nucleic acid sequences (which can comprise regions of sequence variation) are located on the same chromosome and/or the same chromosomal fragment. Phasing information can be obtained by performing multiple, successive sequencing reactions from the same immobilized nucleic acid template. The methods, compositions and kits provided herein can be useful, for example, for haplotyping, SNP phasing, or for determining downstream exons in RNA-seq.

17 Claims, 7 Drawing Sheets

Specification includes a Sequence Listing.

Related U.S. Application Data

(60) Provisional application No. 61/801,600, filed on Mar. 15, 2013.

(56) References Cited

U.S. PATENT DOCUMENTS

| | | |
|---|---|---|
| 4,469,863 A | 9/1984 | Ts'o et al. |
| 4,582,877 A | 4/1986 | Fairchok et al. |
| 4,876,187 A | 10/1989 | Duck et al. |
| 4,925,065 A | 5/1990 | Golias |
| 4,935,357 A | 6/1990 | Szybalski |
| 4,942,124 A | 7/1990 | Church |
| 4,988,617 A | 1/1991 | Landegren et al. |
| 4,996,143 A | 2/1991 | Heller et al. |
| 5,011,769 A | 4/1991 | Duck et al. |
| 5,034,506 A | 7/1991 | Summerton et al. |
| 5,035,996 A | 7/1991 | Hartley |
| 5,043,272 A | 8/1991 | Hartley |
| 5,082,830 A | 1/1992 | Brakel et al. |
| 5,090,591 A | 2/1992 | Long |
| 5,130,238 A | 7/1992 | Malek et al. |
| 5,169,766 A | 12/1992 | Schuster et al. |
| 5,171,534 A | 12/1992 | Smith et al. |
| 5,194,370 A | 3/1993 | Berninger et al. |
| 5,216,141 A | 6/1993 | Benner |
| 5,234,809 A | 8/1993 | Boom et al. |
| 5,235,033 A | 8/1993 | Summerton et al. |
| 5,242,794 A | 9/1993 | Whiteley et al. |
| 5,384,242 A | 1/1995 | Oakes |
| 5,386,023 A | 1/1995 | Sanghvi et al. |
| 5,399,491 A | 3/1995 | Kacian et al. |
| 5,409,818 A | 4/1995 | Davey et al. |
| 5,418,149 A | 5/1995 | Gelfand et al. |
| 5,422,271 A | 6/1995 | Chen et al. |
| 5,427,929 A | 6/1995 | Richards et al. |
| 5,480,784 A | 1/1996 | Kacian et al. |
| 5,494,810 A | 2/1996 | Barany et al. |
| 5,508,169 A | 4/1996 | Deugau et al. |
| 5,508,178 A | 4/1996 | Rose et al. |
| 5,510,270 A | 4/1996 | Fodor et al. |
| 5,525,471 A | 6/1996 | Zeng |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,565,340 A | 10/1996 | Chenchik et al. |
| 5,573,913 A | 11/1996 | Rosemeyer et al. |
| 5,578,832 A | 11/1996 | Trulson et al. |
| 5,589,339 A | 12/1996 | Hampson et al. |
| 5,602,240 A | 2/1997 | De Mesmaeker et al. |
| 5,637,684 A | 6/1997 | Cook et al. |
| 5,641,658 A | 6/1997 | Adams et al. |
| 5,644,048 A | 7/1997 | Yau |
| 5,665,549 A | 9/1997 | Pinkel et al. |
| 5,667,976 A | 9/1997 | Van Ness et al. |
| 5,667,979 A | 9/1997 | Berrens |
| 5,679,512 A | 10/1997 | Laney et al. |
| 5,681,726 A | 10/1997 | Huse et al. |
| 5,683,879 A | 11/1997 | Laney et al. |
| 5,688,648 A | 11/1997 | Mathies et al. |
| 5,705,628 A | 1/1998 | Hawkins |
| 5,708,154 A | 1/1998 | Smith et al. |
| 5,710,028 A | 1/1998 | Eyal et al. |
| 5,712,126 A | 1/1998 | Weissman et al. |
| 5,716,785 A | 2/1998 | Van Gelder et al. |
| 5,726,329 A | 3/1998 | Jones et al. |
| 5,750,341 A | 5/1998 | Macevicz |
| 5,759,822 A | 6/1998 | Chenchik et al. |
| 5,763,178 A | 6/1998 | Chirikjian et al. |
| 5,789,206 A | 8/1998 | Tavtigian et al. |
| 5,824,517 A | 10/1998 | Cleuziat et al. |
| 5,824,518 A | 10/1998 | Kacian et al. |
| 5,837,832 A | 11/1998 | Chee et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,945,313 A | 8/1999 | Hartley et al. |
| 5,952,176 A | 9/1999 | McCarthy et al. |
| 5,958,681 A | 9/1999 | Wetmur et al. |
| 5,965,409 A | 10/1999 | Pardee et al. |
| 5,969,119 A | 10/1999 | Macevicz |
| 5,972,618 A | 10/1999 | Bloch |
| 6,004,744 A | 12/1999 | Goelet et al. |
| 6,004,745 A | 12/1999 | Arnold, Jr. et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,056,661 A | 5/2000 | Schmidt |
| 6,077,674 A | 6/2000 | Schleifer et al. |
| 6,087,103 A | 7/2000 | Burmer |
| 6,090,553 A | 7/2000 | Matson |
| 6,090,591 A | 7/2000 | Burg et al. |
| 6,107,023 A | 8/2000 | Reyes et al. |
| 6,110,709 A | 8/2000 | Ausubel et al. |
| 6,150,112 A | 11/2000 | Weissman et al. |
| 6,159,685 A | 12/2000 | Pinkel et al. |
| 6,160,105 A | 12/2000 | Cunningham et al. |
| 6,169,194 B1 | 1/2001 | Thompson et al. |
| 6,172,208 B1 | 1/2001 | Cook |
| 6,174,680 B1 | 1/2001 | Makrigiorgos |
| 6,180,338 B1 | 1/2001 | Adams |
| 6,190,865 B1 | 2/2001 | Jendrisak et al. |
| 6,194,211 B1 | 2/2001 | Richards et al. |
| 6,197,501 B1 | 3/2001 | Cremer et al. |
| 6,197,557 B1 | 3/2001 | Makarov et al. |
| 6,210,891 B1 | 4/2001 | Nyren et al. |
| 6,225,109 B1 | 5/2001 | Juncosa et al. |
| 6,225,451 B1 | 5/2001 | Ballinger et al. |
| 6,232,104 B1 | 5/2001 | Lishanski et al. |
| 6,251,639 B1 | 6/2001 | Kurn |
| 6,262,490 B1 | 7/2001 | Hsu et al. |
| 6,270,961 B1 | 8/2001 | Drmanac |
| 6,280,935 B1 | 8/2001 | Macevicz |
| 6,287,766 B1 | 9/2001 | Nolan et al. |
| 6,287,825 B1 | 9/2001 | Weissman et al. |
| 6,291,170 B1 | 9/2001 | Van Gelder et al. |
| 6,306,365 B1 | 10/2001 | Ruoslahti et al. |
| 6,306,597 B1 | 10/2001 | Macevicz |
| 6,309,843 B1 | 10/2001 | Timms |
| 6,326,142 B1 | 12/2001 | Royer |
| 6,335,167 B1 | 1/2002 | Pinkel et al. |
| 6,339,147 B1 | 1/2002 | Lukhtanov et al. |
| 6,440,705 B1 | 8/2002 | Stanton, Jr. et al. |
| 6,449,562 B1 | 9/2002 | Chandler et al. |
| 6,582,938 B1 | 6/2003 | Su et al. |
| 6,670,461 B1 | 12/2003 | Wengel et al. |
| 6,686,156 B2 | 2/2004 | Kurn |
| 6,692,918 B2 | 2/2004 | Kurn |
| 6,770,748 B2 | 8/2004 | Imanishi et al. |
| 6,777,180 B1 | 8/2004 | Fisher et al. |
| 6,794,499 B2 | 9/2004 | Wengel et al. |
| 6,815,164 B2 | 11/2004 | Kurn |
| 6,815,167 B2 | 11/2004 | Crothers et al. |
| 6,825,011 B1 | 11/2004 | Romantchikov |
| 6,833,246 B2 | 12/2004 | Balasubramanian |
| 6,849,404 B2 | 2/2005 | Park et al. |
| 6,858,413 B2 | 2/2005 | Kurn |
| 6,913,884 B2 | 7/2005 | Stuelpnagel et al. |
| 6,917,726 B2 | 7/2005 | Levene et al. |
| 6,924,104 B2 | 8/2005 | Weissman et al. |
| 6,946,251 B2 | 9/2005 | Kurn |
| 7,001,724 B1 | 2/2006 | Greenfield |
| 7,033,764 B2 | 4/2006 | Korlach et al. |
| 7,048,481 B2 | 5/2006 | Sugata et al. |
| 7,052,847 B2 | 5/2006 | Korlach et al. |
| 7,056,676 B2 | 6/2006 | Korlach et al. |
| 7,056,716 B2 | 6/2006 | Potter et al. |
| 7,060,441 B2 | 6/2006 | Bourget et al. |
| 7,094,536 B2 | 8/2006 | Kurn |
| 7,115,400 B1 | 10/2006 | Adessi et al. |
| 7,170,050 B2 | 1/2007 | Turner et al. |
| 7,175,982 B1 | 2/2007 | McCarthy et al. |
| 7,176,025 B2 | 2/2007 | Kurn et al. |

(56) References Cited

U.S. PATENT DOCUMENTS

| | | |
|---|---|---|
| 7,189,512 B2 | 3/2007 | Porat et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,273,730 B2 | 9/2007 | Du Breuil Lastrucci |
| 7,276,720 B2 | 10/2007 | Ulmer |
| 7,294,461 B2 | 11/2007 | Kurn |
| 7,300,755 B1 | 11/2007 | Petersdoif et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,351,557 B2 | 4/2008 | Kurn |
| 7,354,717 B2 | 4/2008 | Kurn |
| 7,361,466 B2 | 4/2008 | Korlach et al. |
| 7,361,468 B2 | 4/2008 | Liu et al. |
| 7,402,386 B2 | 7/2008 | Kurn et al. |
| 7,405,281 B2 | 7/2008 | Xu et al. |
| 7,414,117 B2 | 8/2008 | Saito et al. |
| 7,416,844 B2 | 8/2008 | Korlach et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 7,579,153 B2 | 8/2009 | Brenner et al. |
| 7,704,687 B2 | 4/2010 | Wang et al. |
| 7,741,463 B2 | 6/2010 | Gormley et al. |
| 7,771,934 B2 | 8/2010 | Kurn |
| 7,771,946 B2 | 8/2010 | Kurn |
| 7,803,550 B2 | 9/2010 | Makarov et al. |
| 7,846,666 B2 | 12/2010 | Kurn |
| 7,846,733 B2 | 12/2010 | Kurn |
| 7,867,703 B2 | 1/2011 | Sampson et al. |
| 7,939,258 B2 | 5/2011 | Kurn et al. |
| 7,948,015 B2 | 5/2011 | Rothberg et al. |
| 7,985,565 B2 | 7/2011 | Mayer et al. |
| 8,017,335 B2 | 9/2011 | Smith |
| 8,034,568 B2 | 10/2011 | Kurn et al. |
| 8,053,192 B2 | 11/2011 | Bignell et al. |
| 8,071,311 B2 | 12/2011 | Kurn |
| 8,143,001 B2 | 3/2012 | Kurn et al. |
| 8,209,130 B1 | 6/2012 | Kennedy et al. |
| 8,334,116 B2 | 12/2012 | Kurn |
| 8,465,950 B2 | 6/2013 | Kurn et al. |
| 8,492,095 B2 | 7/2013 | Kurn |
| 8,512,956 B2 | 8/2013 | Kurn |
| 8,551,709 B2 | 10/2013 | Kurn et al. |
| 8,852,867 B2 | 10/2014 | Kurn et al. |
| 8,999,677 B1 | 4/2015 | Soldatov et al. |
| 9,175,325 B2 | 11/2015 | Kurn et al. |
| 9,175,336 B2 | 11/2015 | Soldatov et al. |
| 9,181,582 B2 | 11/2015 | Kurn |
| 9,206,418 B2 | 12/2015 | Armour |
| 9,248,076 B2 | 2/2016 | Sullivan et al. |
| 9,546,399 B2 | 1/2017 | Amorese et al. |
| 9,650,628 B2 | 5/2017 | Amorese et al. |
| 9,702,004 B2 | 7/2017 | Van Eijk et al. |
| 9,745,627 B2 | 8/2017 | van Eijk et al. |
| 9,896,721 B2 | 2/2018 | Van Eijk et al. |
| 2001/0000077 A1 | 3/2001 | Engelhardt et al. |
| 2001/0031739 A1 | 10/2001 | Dare |
| 2001/0034048 A1 | 10/2001 | Kurn |
| 2001/0041334 A1 | 11/2001 | Rashtchian et al. |
| 2002/0028447 A1 | 3/2002 | Li et al. |
| 2002/0058270 A1 | 5/2002 | Kurn |
| 2002/0115088 A1 | 8/2002 | Kurn |
| 2002/0150919 A1 | 10/2002 | Weismann et al. |
| 2002/0155451 A1 | 10/2002 | Makrigiorgos |
| 2002/0164628 A1 | 11/2002 | Kurn |
| 2002/0164634 A1 | 11/2002 | Patil et al. |
| 2002/0197639 A1 | 12/2002 | Shia et al. |
| 2003/0017591 A1 | 1/2003 | Kurn |
| 2003/0022207 A1 | 1/2003 | Balasubramanian et al. |
| 2003/0082543 A1 | 5/2003 | Su et al. |
| 2003/0087251 A1 | 5/2003 | Kurn |
| 2003/0119150 A1 | 6/2003 | Ankenbauer et al. |
| 2003/0143555 A1 | 7/2003 | Bourget et al. |
| 2003/0175780 A1 | 9/2003 | Jones |
| 2003/0180779 A1 | 9/2003 | Lofton-Day et al. |
| 2003/0186234 A1 | 10/2003 | Kurn |
| 2003/0207279 A1 | 11/2003 | Crothers et al. |
| 2003/0211616 A1 | 11/2003 | Leong |
| 2003/0215926 A1 | 11/2003 | Kurn et al. |
| 2003/0224439 A1 | 12/2003 | Lafferty et al. |
| 2003/0232348 A1 | 12/2003 | Jones et al. |
| 2004/0002371 A1 | 1/2004 | Paquin et al. |
| 2004/0005614 A1 | 1/2004 | Kurn et al. |
| 2004/0023271 A1 | 2/2004 | Kurn et al. |
| 2004/0115815 A1 | 6/2004 | Li et al. |
| 2004/0137456 A1 | 7/2004 | Yokota et al. |
| 2004/0161742 A1 | 8/2004 | Dean et al. |
| 2004/0203019 A1 | 10/2004 | Kurn |
| 2004/0203025 A1 | 10/2004 | Kurn |
| 2004/0248153 A1 | 12/2004 | Dear et al. |
| 2005/0003441 A1 | 1/2005 | Kurn |
| 2005/0014192 A1 | 1/2005 | Kurn |
| 2005/0019793 A1 | 1/2005 | Kurn et al. |
| 2005/0059048 A1 | 3/2005 | Gunderson et al. |
| 2005/0064456 A1 | 3/2005 | Kurn |
| 2005/0123956 A1 | 6/2005 | Blume et al. |
| 2005/0136417 A1 | 6/2005 | Cole et al. |
| 2005/0142577 A1 | 6/2005 | Jones et al. |
| 2005/0191656 A1 | 9/2005 | Drmanac et al. |
| 2005/0191682 A1 | 9/2005 | Barone et al. |
| 2005/0208538 A1 | 9/2005 | Kurn et al. |
| 2006/0008824 A1 | 1/2006 | Ronaghi et al. |
| 2006/0014182 A1 | 1/2006 | Kurn |
| 2006/0024678 A1 | 2/2006 | Buzby |
| 2006/0024711 A1 | 2/2006 | Lapidus et al. |
| 2006/0035274 A1 | 2/2006 | Dong |
| 2006/0046251 A1 | 3/2006 | Sampson et al. |
| 2006/0051789 A1 | 3/2006 | Kazakov et al. |
| 2006/0068415 A1 | 3/2006 | Jones et al. |
| 2006/0134633 A1 | 6/2006 | Chen et al. |
| 2006/0216724 A1 | 9/2006 | Christians et al. |
| 2006/0263789 A1 | 11/2006 | Kincaid |
| 2006/0281082 A1 | 12/2006 | Zhu |
| 2006/0286566 A1 | 12/2006 | Lapidus et al. |
| 2006/0292597 A1 | 12/2006 | Shapero et al. |
| 2007/0031857 A1 | 2/2007 | Makarov et al. |
| 2007/0134128 A1 | 6/2007 | Korlach |
| 2007/0141604 A1 | 6/2007 | Gormley et al. |
| 2007/0224607 A1 | 9/2007 | Morgan et al. |
| 2007/0224613 A1 | 9/2007 | Strathmann |
| 2007/0231823 A1 | 10/2007 | McKernan et al. |
| 2007/0238122 A1 | 10/2007 | Allbritton et al. |
| 2007/0263045 A1 | 11/2007 | Okazawa |
| 2008/0038727 A1 | 2/2008 | Spier |
| 2008/0087826 A1 | 4/2008 | Harris et al. |
| 2008/0103058 A1 | 5/2008 | Siddiqi |
| 2008/0131937 A1 | 6/2008 | Schroeder |
| 2008/0160580 A1 | 7/2008 | Adessi et al. |
| 2008/0176311 A1 | 7/2008 | Kurn |
| 2008/0182300 A1 | 7/2008 | Kurn |
| 2008/0194413 A1 | 8/2008 | Albert |
| 2008/0194416 A1 | 8/2008 | Chen |
| 2008/0206764 A1 | 8/2008 | Williams et al. |
| 2008/0213770 A1 | 9/2008 | Williams et al. |
| 2008/0217246 A1 | 9/2008 | Benn et al. |
| 2008/0241831 A1 | 10/2008 | Fan et al. |
| 2008/0242560 A1 | 10/2008 | Gunderson et al. |
| 2008/0286795 A1 | 11/2008 | Kawashima et al. |
| 2009/0011959 A1 | 1/2009 | Costa et al. |
| 2009/0024331 A1 | 1/2009 | Tomaney et al. |
| 2009/0026082 A1 | 1/2009 | Rothberg et al. |
| 2009/0029385 A1 | 1/2009 | Christians et al. |
| 2009/0036663 A1 | 2/2009 | Kurn |
| 2009/0061425 A1 | 3/2009 | Lo et al. |
| 2009/0061439 A1 | 3/2009 | Buzby |

(56) References Cited

U.S. PATENT DOCUMENTS

| | | |
|---|---|---|
| 2009/0068645 A1 | 3/2009 | Sibson |
| 2009/0068655 A1 | 3/2009 | Williams |
| 2009/0068709 A1 | 3/2009 | Kurn et al. |
| 2009/0105081 A1 | 4/2009 | Rodesch et al. |
| 2009/0117573 A1 | 5/2009 | Fu et al. |
| 2009/0117621 A1 | 5/2009 | Boutell et al. |
| 2009/0123923 A1 | 5/2009 | Yamamoto et al. |
| 2009/0124514 A1 | 5/2009 | Fu et al. |
| 2009/0127589 A1 | 5/2009 | Rothberg et al. |
| 2009/0130721 A1 | 5/2009 | Kurn et al. |
| 2009/0203085 A1 | 8/2009 | Kurn et al. |
| 2009/0203531 A1 | 8/2009 | Kurn |
| 2009/0233802 A1 | 9/2009 | Bignell et al. |
| 2009/0233804 A1 | 9/2009 | Kurn et al. |
| 2009/0239232 A1 | 9/2009 | Kurn |
| 2009/0275486 A1 | 11/2009 | Kurn et al. |
| 2009/0280538 A1 | 11/2009 | Patel et al. |
| 2009/0298075 A1 | 12/2009 | Travers et al. |
| 2010/0015666 A1 | 1/2010 | Brenner et al. |
| 2010/0021973 A1 | 1/2010 | Makarov et al. |
| 2010/0022403 A1 | 1/2010 | Kurn et al. |
| 2010/0029511 A1 | 2/2010 | Raymond et al. |
| 2010/0081174 A1 | 4/2010 | Dunn |
| 2010/0105052 A1 | 4/2010 | Drmanac et al. |
| 2010/0113296 A1 | 5/2010 | Myerson |
| 2010/0129879 A1 | 5/2010 | Ach et al. |
| 2010/0137143 A1 | 6/2010 | Rothberg et al. |
| 2010/0159559 A1 | 6/2010 | Kurn et al. |
| 2010/0167954 A1 | 7/2010 | Earnshaw et al. |
| 2010/0173394 A1 | 7/2010 | Colston, Jr. et al. |
| 2010/0203597 A1 | 8/2010 | Chen et al. |
| 2010/0267043 A1 | 10/2010 | Braverman et al. |
| 2010/0273219 A1 | 10/2010 | May et al. |
| 2010/0311066 A1 | 12/2010 | Kurn |
| 2010/0323348 A1 | 12/2010 | Hamady et al. |
| 2011/0009276 A1* | 1/2011 | Vermaas .............. C12Q 1/6874 506/7 |
| 2011/0015096 A1 | 1/2011 | Chiu |
| 2011/0039732 A1 | 2/2011 | Raymond et al. |
| 2011/0104785 A1 | 5/2011 | Vaidyanathan et al. |
| 2011/0105364 A1 | 5/2011 | Kurn |
| 2011/0129827 A1 | 6/2011 | Causey et al. |
| 2011/0189679 A1 | 8/2011 | Kurn et al. |
| 2011/0224105 A1 | 9/2011 | Kurn et al. |
| 2011/0288780 A1 | 11/2011 | Rabinowitz et al. |
| 2011/0294132 A1 | 12/2011 | Kurn |
| 2011/0319290 A1 | 12/2011 | Raymond et al. |
| 2012/0003657 A1 | 1/2012 | Myllykangas et al. |
| 2012/0028310 A1 | 2/2012 | Kurn et al. |
| 2012/0045797 A1 | 2/2012 | Kurn et al. |
| 2012/0071331 A1 | 3/2012 | Casbon et al. |
| 2012/0074925 A1 | 3/2012 | Oliver |
| 2012/0102054 A1 | 4/2012 | Popescu et al. |
| 2012/0107811 A1 | 5/2012 | Kelso et al. |
| 2012/0122701 A1 | 5/2012 | Ryan et al. |
| 2012/0149068 A1 | 6/2012 | Kurn |
| 2012/0156728 A1 | 6/2012 | Li et al. |
| 2012/0157322 A1 | 6/2012 | Myllykangas et al. |
| 2012/0190587 A1 | 7/2012 | Kurn et al. |
| 2012/0208705 A1 | 8/2012 | Steemers et al. |
| 2012/0220483 A1 | 8/2012 | Kurn et al. |
| 2012/0220494 A1 | 8/2012 | Samuels et al. |
| 2012/0237943 A1 | 9/2012 | Soldatov et al. |
| 2012/0238738 A1 | 9/2012 | Hendrickson |
| 2012/0245041 A1 | 9/2012 | Brenner et al. |
| 2012/0252682 A1* | 10/2012 | Zhou .............. C12Q 1/6869 506/7 |
| 2012/0270212 A1 | 10/2012 | Rabinowitz et al. |
| 2012/0283145 A1 | 11/2012 | Wang |
| 2012/0289426 A1 | 11/2012 | Roos et al. |
| 2012/0309002 A1 | 12/2012 | Link |
| 2013/0005585 A1 | 1/2013 | Anderson et al. |
| 2013/0059738 A1 | 3/2013 | Leamon et al. |
| 2013/0231253 A1 | 9/2013 | Amorese et al. |
| 2014/0038188 A1 | 2/2014 | Kurn |
| 2014/0038236 A1 | 2/2014 | Kurn et al. |
| 2014/0065692 A1 | 3/2014 | Kurn et al. |
| 2014/0274729 A1 | 9/2014 | Kurn et al. |
| 2014/0274731 A1 | 9/2014 | Raymond et al. |
| 2014/0274738 A1 | 9/2014 | Amorese et al. |
| 2014/0303000 A1 | 10/2014 | Armour |
| 2014/0378345 A1 | 12/2014 | Hindson et al. |
| 2015/0004600 A1 | 1/2015 | Wang et al. |
| 2015/0011396 A1 | 1/2015 | Schroeder et al. |
| 2015/0017635 A1 | 1/2015 | Myllykangas et al. |
| 2015/0037790 A1 | 2/2015 | Fox et al. |
| 2015/0101595 A1 | 4/2015 | Hancock et al. |
| 2015/0133319 A1 | 5/2015 | Fu et al. |
| 2015/0284769 A1 | 10/2015 | Schroeder |
| 2015/0299767 A1 | 10/2015 | Armour et al. |
| 2015/0299784 A1 | 10/2015 | Fan et al. |
| 2015/0299812 A1 | 10/2015 | Talasaz |
| 2016/0016140 A1 | 1/2016 | Jovanovich et al. |
| 2016/0122756 A1 | 5/2016 | Armour |
| 2016/0130576 A1 | 5/2016 | Armour |
| 2016/0153039 A1 | 6/2016 | Amorese et al. |
| 2016/0203259 A1 | 7/2016 | Scolnick et al. |
| 2016/0220994 A1 | 8/2016 | Wright |
| 2016/0251711 A1 | 9/2016 | Amorese et al. |
| 2016/0265042 A1 | 9/2016 | Schroeder et al. |
| 2016/0275240 A1 | 9/2016 | Huelga et al. |
| 2016/0296930 A1 | 10/2016 | Matear et al. |

FOREIGN PATENT DOCUMENTS

| | | |
|---|---|---|
| CN | 101565746 A | 10/2009 |
| CN | 105890722 A | 8/2016 |
| EP | 0365627 B1 | 12/1993 |
| EP | 0329822 B1 | 6/1994 |
| EP | 0667393 A2 | 8/1995 |
| EP | 1071811 B1 | 3/2002 |
| EP | 0843735 B1 | 7/2002 |
| EP | 2272976 A1 | 1/2011 |
| EP | 2322612 A1 | 5/2011 |
| EP | 2451973 A1 | 5/2012 |
| EP | 2511381 A1 | 10/2012 |
| EP | 1929039 B2 | 11/2013 |
| WO | 89/09284 A1 | 10/1989 |
| WO | 92/07951 A1 | 5/1992 |
| WO | 93/18052 A1 | 9/1993 |
| WO | 94/16090 A1 | 7/1994 |
| WO | 96/40998 A1 | 12/1996 |
| WO | 97/12061 A1 | 4/1997 |
| WO | 97/25416 A2 | 7/1997 |
| WO | 98/06736 A1 | 2/1998 |
| WO | 98/38296 A1 | 9/1998 |
| WO | 98/044151 A1 | 10/1998 |
| WO | 99/10540 A1 | 3/1999 |
| WO | 99/11819 A1 | 3/1999 |
| WO | 99/42618 A1 | 8/1999 |
| WO | 00/08208 A2 | 2/2000 |
| WO | 2000/09756 A1 | 2/2000 |
| WO | 00/018957 A1 | 4/2000 |
| WO | 00/39345 A1 | 7/2000 |
| WO | 2000/043531 A2 | 7/2000 |
| WO | 00/52191 A1 | 9/2000 |
| WO | 2000/55364 A2 | 9/2000 |
| WO | 00/70039 A1 | 11/2000 |
| WO | 01/20035 A2 | 3/2001 |
| WO | 01/23613 A1 | 4/2001 |
| WO | 01/46464 A1 | 6/2001 |
| WO | 01/57248 A2 | 8/2001 |
| WO | 01/64952 A2 | 9/2001 |
| WO | 02/00938 A2 | 1/2002 |
| WO | 02/28876 A2 | 4/2002 |
| WO | 02/29117 A2 | 4/2002 |
| WO | 02/36821 A2 | 5/2002 |
| WO | 02/48402 A2 | 6/2002 |
| WO | 02/060318 A2 | 8/2002 |
| WO | 02/072772 A2 | 9/2002 |
| WO | 02/072773 A2 | 9/2002 |
| WO | 02/081753 A1 | 10/2002 |
| WO | 02/090584 A2 | 11/2002 |
| WO | 03/004690 A2 | 1/2003 |

(56) References Cited

FOREIGN PATENT DOCUMENTS

| | | |
|---|---|---|
| WO | 2003/002736 A2 | 1/2003 |
| WO | 2003/012118 A1 | 2/2003 |
| WO | 03/027259 A2 | 4/2003 |
| WO | 03/078645 A2 | 9/2003 |
| WO | 03/083435 A2 | 10/2003 |
| WO | 03/106642 A2 | 12/2003 |
| WO | 04/011665 A2 | 2/2004 |
| WO | 2004/070007 A2 | 8/2004 |
| WO | 2004/092418 A2 | 10/2004 |
| WO | 2005/003375 A2 | 1/2005 |
| WO | 2005/003381 A1 | 1/2005 |
| WO | 2005/038427 A2 | 4/2005 |
| WO | 2005/065321 A2 | 7/2005 |
| WO | 2006/081222 A2 | 8/2006 |
| WO | 2006/086668 A2 | 8/2006 |
| WO | 2006/137733 A1 | 12/2006 |
| WO | 2007/018601 A1 | 2/2007 |
| WO | 2007/019444 A2 | 2/2007 |
| WO | 2007/030759 A2 | 3/2007 |
| WO | 2007/037678 A2 | 4/2007 |
| WO | 2007/052006 A1 | 5/2007 |
| WO | 2007/057652 A1 | 5/2007 |
| WO | 2007/073165 A1 | 6/2007 |
| WO | 2007/136717 A1 | 11/2007 |
| WO | 2008/005459 A2 | 1/2008 |
| WO | 2008/015396 A2 | 2/2008 |
| WO | 2008/033442 A2 | 3/2008 |
| WO | 2008/093098 A2 | 8/2008 |
| WO | 2008/115185 A2 | 9/2008 |
| WO | 2008150432 A1 | 12/2008 |
| WO | 2009/053039 A1 | 4/2009 |
| WO | 2009/102878 A2 | 8/2009 |
| WO | 2009/102896 A2 | 8/2009 |
| WO | 2009/112844 A1 | 9/2009 |
| WO | 2009/117698 A2 | 9/2009 |
| WO | 2009/120372 A2 | 10/2009 |
| WO | 2009/120374 A2 | 10/2009 |
| WO | 2010/003153 A2 | 1/2010 |
| WO | 2010/030683 A1 | 3/2010 |
| WO | 2010/039991 A2 | 4/2010 |
| WO | 2010/063711 A1 | 6/2010 |
| WO | 2010/064893 A1 | 6/2010 |
| WO | 2010/085715 A1 | 7/2010 |
| WO | 2010/091246 A2 | 8/2010 |
| WO | 2010/115154 A1 | 10/2010 |
| WO | 2010/129937 A2 | 11/2010 |
| WO | 2011/003630 A1 | 1/2011 |
| WO | 2011/009941 A1 | 1/2011 |
| WO | 2011/019964 A1 | 2/2011 |
| WO | 2011/032053 A1 | 3/2011 |
| WO | 2011032040 A1 | 3/2011 |
| WO | 2011/053987 A1 | 5/2011 |
| WO | 2011/151777 A1 | 12/2011 |
| WO | 2011/156529 A2 | 12/2011 |
| WO | 2012/013932 A1 | 2/2012 |
| WO | 2012/061832 A1 | 5/2012 |
| WO | 2012/054873 A3 | 8/2012 |
| WO | 2012/103154 A1 | 8/2012 |
| WO | 2013/059740 A1 | 4/2013 |
| WO | 2013/059746 A1 | 4/2013 |
| WO | 2013/112923 A1 | 8/2013 |
| WO | 2013/130512 A3 | 10/2013 |
| WO | 2013/177220 A1 | 11/2013 |
| WO | 2013/190441 A2 | 12/2013 |
| WO | 2013/191775 A2 | 12/2013 |
| WO | 2014/039556 A1 | 3/2014 |
| WO | 2014/082032 A1 | 5/2014 |
| WO | 2013/138510 A9 | 7/2014 |
| WO | 2014/144092 A1 | 9/2014 |
| WO | 2014/150931 A1 | 9/2014 |
| WO | 2015/031691 A1 | 3/2015 |
| WO | 2015/073711 A1 | 5/2015 |
| WO | 2015/104302 A1 | 7/2015 |
| WO | 2015/131107 A1 | 9/2015 |

OTHER PUBLICATIONS

Browning, S.R. et al., Haplotype phasing: existing methods and new developments, Nature Rev. Gen., vol. 12, pp. 703-714 (Year: 2011).*
Westin 2000, Anchored multiplex amplification on a microelectronic chip array, Nat Biotech 18:199-204.
Wienholds, 2004, Target-selected gene inactivation in zebrafish, Meth Cell Biol 77:69-90.
Wolford, 2000, High-throughput SNP detection by using DNA pooling and denaturing high performance liquid chromatography (DHPLC), Hum Genet 107:483-487.
Xi, 2011, Copy number variation detection in whole-genome sequencing data using the Bayesian information criterion, PNAS 108(46):e1128-e1136.
Xu, 2012, FastUniq: A fast de novo duplicates removal tool for paired short reads, PLoSOne 7(12):e52249.
Applied Biosystems, 2010, BigDye Terminator v3.1 Cycle Sequencing Kit Protocol (72 pages).
Baldwin, 2009, Multilocus sequence typing of Cronobacter sakazakii and Cronobacter malonaticus reveals stable alonal structures with clinical significance which do not correlate with biotypes, BMC Microbiol 9(223):1-9.
Amos, 2000, DNA pooling in mutation detection with reference to sequence analysis, Am J Hum Genet 66:1689-1692.
Bellos, 2014, cnvCapSeq: detecting copy number variation in long-range targeted resequencing data, Nucleic Acids Res 42(20):e158.
Benson, 2013, Genbank, Nucl Acids Res 41:D36-D42.
Blomquist, 2013, Targeted RNA-Sequencing with Competitive Multiplex-PCR Amplicon Libraries, PLOS ONE 8(11): e79120.
Bodi, 2013, Comparison of commercially available target enrichment methods for next-generation sequencing, J Biomolecular Tech 24:73-86.
Church, 1988, Multiplexed DNA sequencing, Science 240:185-188.
Colbert, 2001, High-throughput screening for induced point mutations, Plant Physiol 126:480-484.
Collard, 2005, An introduction to markers, quantitative trait loci (QTL) mapping and marker-assisted selection for crop improvements: the basic concepts Euphytica 142:169-196.
Eminaga, 2013, Quantification of microRNA Expression with Next-Generation Sequencing, Unit 4.17 in Current Protocols in Molecular Biology, Wiley, New York, NY (14 pages).
Fakhrai-Rad, 2002, Pyroseqeuncing: an accurate detection platform for single nucleotide polymorphisms, Human Mutation 19:479-485.
Grothues, 1993, PCR amplification of megabase DNA with tagged random primers (T-PCR), Nucl Acids Res 21:1321-1322.
Hajibabaei, 2005, Critical factors for assembling a high volume of DNA barcodes, Phil Trans R Soc B 360:1959-1967.
Illumina, 2011, TruSeq RNA and DNA Sample Preparation Kits v2, 1-15 Illumina, dated 27 Apr. 27, 2011 (4 pages).
International Search Report and Written Opinion dated Jan. 6, 2016, for PCT/US15/44065, filed Aug. 6, 2015 (21 pages).
International Search Report and Written Opinion dated Jul. 10, 2017, for Application No. PCT/US17/27060, filed Apr. 11, 2017 (9 pages).
International Search Report and Written Opinion dated Mar. 5, 2015, in international patent application PCT/US2014/065530, filed Nov. 13, 2014 (12 pages).
Ion Total RNA-Seq Kit v2, User Guide, 2012, Life Technologies (82 pages).
Jiang, 2015, CODEX: a normalization and copy number variation detection method for whole exome sequencing, Nucleic Acids Res 43(6):e39.
Krumm, 2012, Copy number variation detection and genotyping from exome sequence data, Genome Res 22 (8):1525-1532.
Lai 2004, Characterization of the maize endosperm transcriptome and its comparison to the rice genome, Genome Res14:1932-1937.
Langmead, 2009, Ultrafast and memory-efficient alignment of short DNA sequences to the human genome, Genome Biol 10:R25.
Li, 2012, CONTRA: copy number analysis for targeted resequencing, Bioinformatics 28(10):1307-1313.

(56) References Cited

OTHER PUBLICATIONS

Lindstrom, 2004, Pyrosequencing for detection of Lamivudine-resistant Hepatitis B virus, J Clin Microb 42 (10):4788-4795.
Liu 2008, Sequence space coverage, entropy of genomes and the potential to detect non-human DNA in human samples, BMC Genomics 9(509):1-17.
Ma, 2015, Quantitative Analysis of Copy Number Variants Based on Real-Time LightCycler PCR, Curr Protoc Hum Genet 80:7.21.1-7.23.8.
Machine translation generated on Mar. 7, 2018, of CN 105890722 by website of European Patent Office (4 pages).
Margulies, 2005, Genome sequencing in open microfabricated high density picoliter reactors, Nature 437 (7057):376-380.
McCloskey, 2007, Encoding PCR products with batch-stamps and barcodes, Biochem Genet 45:761-767.
Miner, 2004, Molecular barcodes detect redundancy and contamination in hairpin-bisulfite PCR, Nucl Acids Res 32 (17):e135.
Myers, 2013, Protocol for Creating Multiplexed miRNA Libraries for Use in Illumina Sequencing, Myers lab microRNA-seq Protocol, Hudson Alpha Institute for Biotechnology web site, dated May 2, 2013, (15 pages).
NuGEN, 2014, User Guide Ovation Target Enrichment System, NuGEN Technologies Inc., San Carlos, CA (45 pages).
Plagnol, 2012, A robust model for read count data in exome sequencing experiments and implications for copy number variant calling, Bioinformatics 28(21):2747-2754.
Qiu, 2003, DNA sequence-based "bar-codes" for tracking the origins of expressed sequence tags from a maize cDNA library constructed using multiple mRNA sources, Plant Physiol 133:475-481.
Querfurth, 2012, Creation and application of immortalized bait libraries for targeted enrichment and next-generation sequencing, Biotechniques 52(6):375-380.
Ronaghi, 2001, Pyrosequencing sheds light on DNA sequencing, Genome Res 11:3-11.
Sathirapongsasuti, 2011, Exome sequencing-based copy-No. variation and loss of heterozygosity detection: ExomeCNV, Bioinformatics 27(19):2648-2654.
Schiemer, 2011, Illumina TruSeq Adapters Demystified,Tufts University Core Facility XP055357867 (5 pages).
Shapero, 2001, SNP Genotyping by multiplexed solid-phase amplification and fluorescent minisequencing, Genome Res 11:1926-1934.
Shendure, 2005, Accurate multiplex polony sequencing of an evolved bacterial genome, Science 309:1728.
Boni, 2007, Progress toward ultrafast DNA sequencing using solid-state nanopores, Clin Chem 53(11):1996-2001.
Sood, 2006, Methods for reverse genetic screening in zebrafish by resequencing and TILLING, Methods 39:220-227.
Staroscik, 2004, Calculator for determining the number of copies of a template, URI Genomics, webpage archive dated Apr. 6, 2017 (1 page), Retreived from the internet on Mar. 7, 2018, from <https://web.archive.org/web/20170406174850/http://cels.uri.edu/gsc/cndna.html>.
Stratagene, 1998, Gene characterization kits, Stratagene Catalog, p. 39 (2 pages).
Supplementary European search report and opinion dated Jan. 30, 2018, for European patent application No. 15830393.3 (6 pages).
Till, 2003, Large-scale discovery of induced point mutations with high-throughput TILLING, Genome Res 13:524-530.
Trapnell, 2010, Transcript assembly and quantification by RNA-Seq reveals unannotated transcripts and isoform switching during cell differentiation, Nat Biotech 28:511-515.
Trapnell, 2013, Differential analysis of gene regulation at transcript resolution with RNA-seq, Nat Biotech 31:46-53.
Unemo, 2004, Molecular typing of Neisseria gonorrhoeae isolates by pyrosequencing of highly polymorphic segments of the porB gene, J Clin Microb 42(7):2926-2934.
Vigal, 2002, A review on SNP and other types of molecular markers and their use in animal genetics, Genet Sel Evol 34:275-305.
Walker, 1992, Strand displacement amplification—an isothermal, in vitro DNA amplification technique, Nucl Acids Res 20(7):1691-1696.
Browning, 2011, Haplotype phasing: existing methods and new developments, Nature Rev Gen, 12(10):703-714.
Frederico, 1990, A sensitive genetic assay for the detection of cytosine deamination: determination of rate constants and the activation energy, Biochemistry 29(10):2532-2537.
Genereux, 2008, Errors in the bisulfite conversion of DNA: modulating inappropriate and failed conversion frequencies, Nucl Acids Res 36(22):e150.
International Search Report and Written Opinion dated Jan. 3, 2019, for PCT/US2018/056485, filed Oct. 18, 2018 (11 pages).
International Search Report and Written Opinion dated Jun. 7, 2019, for PCT/US19/22527, filed Mar. 15, 2019 (15 pages).
International Search Report and Written Opinion dated Dec. 14, 2018, for PCT/US2018/056717, filed Oct. 19, 2018.
Mauk, 2018, Simple Approaches to Minimally-Instrumented, Microfluidic-Based Point-of-Care Nucleic Acid Amplification Tests, Biosensors 8(1):e17.
Merriman, 2012, Progress in Ion Torrent semiconductor chip based sequencing, Electrophoresis, 35(23):3397-3417.
Nugen, 2016, Ovation RNA-Seq User Guide, NuGEN Technologies, Inc., San Carlos, CA (42 pages).
Steffens, 2017, A versatile and low-cost open source pipetting robot for automation of toxicological and ecotoxicological bioassays, PLoS One 12(6):e0179636.

* cited by examiner

SEQUENTIAL SEQUENCING

CROSS-REFERENCE

This application claims the benefit of U.S. Non-provisional application Ser. No. 14/778,564, filed Sep. 18, 2015, which is a National Stage of International Application No. PCT/US14/28356 filed Mar. 14, 2014. which claims the benefit of U.S. Provisional Application No. 61/801,600, filed Mar. 15, 2013, all of which are incorporated herein by reference in their entirety.

SEQUENCE LISTING

The instant application contains a Sequence Listing, which has been submitted electronically in ASCII format and is hereby incorporated by reference in its entirety. The ASCI file, created on Nov. 10, 2017, is named NUGN-762-04US-Seq-List_ST25.txt and is 514 bytes in size.

BACKGROUND

Next generation sequencing (NGS) can be utilized for a wide variety of life science applications, such as, e.g., diagnostics, epidemiology, and forensics. Widely used NGS technologies commonly involve sequencing of short reads (e.g., 100 nt reads) which can then be mapped to a reference genome. While such technologies can be useful for the detection of sequence variants (e.g., mutations), they are also associated with certain limitations. For example, NGS can be used to sequence genomes or genomic regions of diploid organisms. A genome of a diploid organism can comprise sets of chromosome pairs, wherein each chromosome pair comprises a maternal chromosome and a paternal chromosome. For example, a diploid organism can inherent a maternal allele and a paternal allele at a single locus. Thus, alleles detected at a plurality of loci which map to a particular chromosome might exist within a single chromosome (maternal or paternal) of a chromosome pair, or across both chromosomes of a chromosome pair. While many NGS platforms are useful for detecting alleles at a plurality of loci, they currently do not provide phasing and/or haplotype information e.g., to distinguish whether alleles detected at a plurality of loci that map to a particular chromosome are co-located on the same chromosome or are located on separate chromosomes in a chromosome pair. Determining whether a plurality of alleles are co-located on the same (maternal or paternal) chromosome or are located on different chromosomes can be useful for a variety of reasons, as discussed further below.

The pattern of alleles within each individual chromosome can be referred to as haplotype. Haplotyping can have many diagnostic and clinical applications. For example, two inactivating mutations across different loci within a single gene might be of little or no consequence if present on the same individual chromosome (i.e. chromosome of either maternal or paternal origin), because the other copy of the gene product will remain functional. On the other hand, if one of the inactivating mutations is present in the maternal chromosome and the other in the paternal chromosome, there can be no functional copy of the gene product, which can result in a negative phenotype (non-viability, increased risk for disease and others). Haplotyping can also be used to predict risk or susceptibility to specific genetic diseases, as many genetic associations are tied to haplotypes. For example, the various haplotypes of the human leukocyte antigen (HLA) system can be associated with genetic diseases ranging from autoimmune disease to cancers.

Another instance in which phasing information can be useful is distinguishing between functional genes and their non-functional pseudogene counterparts within the genome. One well known functional gene/pseudogene pair is the genes SMN1 and SMN2, which differ in sequence by only five nucleotides over many Kb of sequence, yet one of the nucleotide differences renders the SMN2 gene almost completely non-functional. Using short read sequencing, a mutation may be found in one of the two genes, but unless the mutation happens to occur within the sequencing read that also covers one of the known nucleotide differences between SMN1 and SMN2, it will be difficult to know which of the genes (the functional gene, or the nonfunctional pseudogene) is mutated.

The present NGS methods can employ short read sequencing to query regions of variable DNA sequence (polymorphisms etc.) interspersed within regions of conserved DNA sequence. As significant blocks of conserved sequence can be interspersed between the variable regions, short read sequencing does not lend itself to phasing analysis. Although methods have been developed to obtain phasing information, these methods (for example, Sanger sequencing and subcloning), can be labor intensive and/or costly.

There is a need for improved NGS methods that provide phasing information. Such methods can provide a highly parallel platform for performing multiple sequencing reactions from the same immobilized templates. Methods described herein fulfill this need.

SUMMARY OF THE INVENTION

Provided herein are novel methods, compositions and kits for phasing two or more nucleic acid sequences in a sample. Specifically, in one aspect methods and compositions are provided that can allow for determining whether two or more nucleic acid sequences (typically comprising regions of sequence variation) are located on the same nucleic acid template, chromosome, or chromosomal fragment. The methods and compositions disclosed herein can also be used to distinguish and differentiate between two closely related nucleic acid sequences by compiling and aligning data from sequential sequencing reads.

The methods, kits, and compositions described herein can employ sequential paired sequencing reads from the same immobilized nucleic acid template. The reads can be generated by successive rounds of priming, sequencing, denaturing and repriming, and the results from multiple reads originating from the same template can be compiled to obtain phasing information.

Additionally, the methods, kits, and compositions described herein can employ pools of oligonucleotides which may be used to prime sequencing reactions. Such sequencing reactions can target specific regions of specific nucleic acids for sequencing. These oligonucleotide pools can be used onboard a sequencer to extend the sequencing of nucleic acids that have already undergone a first round of sequencing.

In one aspect, provided herein is a method for relating multiple nucleic acid sequences (e.g., comprising regions of sequence variation) to the same nucleic acid template. In some embodiments, the method comprises: a) creating a nucleic acid library; b) sequencing the library with an oligonucleotide primer; c) denaturing the extension strand; d) performing a second round of sequencing by introducing a new oligonucleotide primer containing sequence complementary to conserved regions present in some of the nucleic acid templates within the nucleic acid library; e) repeating steps c) and d) as needed; and f) compiling sequencing data from the successive sequencing reads to differentiate between closely related nucleic acid sequences. In some embodiments, the nucleic acid library is a directional nucleic acid library. In some embodiments, the nucleic acid library is not a directional nucleic acid library.

In some embodiments, the nucleic acid library comprises closely related nucleic acid sequences as inserts. In some embodiments, the conserved regions within the nucleic acid inserts are located adjacent to variable regions. In some embodiments, alignment of multiple variable regions enables differentiating between and/or typing of related transcripts. In some embodiments, alignment of multiple variable regions enables differentiating between and/or typing of related micro-organisms. In some embodiments, the nucleic acid library is a directional nucleic acid library. In some embodiments, the nucleic acid library is not a directional nucleic acid library.

In another aspect, provided herein is a method for differentiating between closely related nucleic acid sequences (such as genes and pseudogenes) by using specific sets of oligonucleotide primers containing sequence complementary to a common region shared by the closely related sequences. In some embodiments, the method comprises: a) creating a sequencing library with related nucleic acid sequences as inserts; b) sequencing the library with an oligonucleotide primer; c) denaturing the extension strand; d) performing a second round of sequencing by introducing a new oligonucleotide primer containing sequence complementary to conserved regions present in some of the nucleic acid templates within the nucleic acid library; e) repeating steps c) and d) as needed; and f) compiling sequencing data from the successive sequencing reads to differentiate between closely related nucleic acid sequences.

Kits for performing any of the methods described herein are provided. Such kits can include reagents, enzymes and platforms for amplification and sequencing of nucleic acids. In one embodiment, a kit is provided comprising: a) an adaptor or several adaptors, b) one or more of oligonucleotide primers, and c) reagents for amplification. In another embodiment, the kit further comprises reagents for sequencing. A kit can include instructions for employing the kit components as well as the use of any other reagent not included in the kit.

Also provided herein is a method for relating at least two nucleic acid sequences or regions of sequence variation to the same nucleic acid template, the method comprising: (a) creating a nucleic acid library wherein a template is immobilized on a solid support; (b) generating a first sequencing read from the immobilized template with a first oligonucleotide primer, wherein a 3' terminal nucleotide of the first oligonucleotide primer binds to a first binding site in the template; (c) denaturing the first sequencing read from the immobilized template; (d) annealing a second oligonucleotide primer that is complementary to a region or regions within the immobilized template, wherein a 3' terminal nucleotide of the second oligonucleotide primer binds to a second binding site in the template that is more than 5 nt away from the first binding site in the template; (e) generating a second sequencing read with the second oligonucleotide primer; and (f) compiling data from the first sequencing read and the second sequencing read to map reads originating from the template. In some embodiments, the nucleic acid libraries are generated from amplicons. In some embodiments, the amplicons comprise conserved regions which flank a variable region. In some embodiments, alignment of multiple variable regions enables differentiation and/or typing of related transcripts. In some embodiments, alignment of multiple variable regions enables differentiation and/or typing of related micro-organisms. In some embodiments, the libraries are reduced complexity. In some embodiments, the reduced complexity is achieved by target enrichment. In some embodiments, the nucleic acid library comprises closely related nucleic acid sequences as inserts. In some embodiments, the nucleic acid library is a directional nucleic acid library. In some embodiments, the nucleic acid library is not a directional nucleic acid library.

Also provided herein is a method comprising: (a) coupling at least one nucleic acid template to a sequencing platform; (b) subjecting the at least one nucleic acid template to a first round of sequencing using a first sequencing primer, wherein the first sequencing primer comprises a 3' terminal nucleotide which anneals to a first binding site in the at least one nucleic acid template, wherein the first round of sequencing produces a first sequencing read of said at least one nucleic acid template; (c) removing said first annealed sequencing primer and said first sequencing read from said at least one nucleic acid template; and (d) subjecting said at least one nucleic acid template to a second round of sequencing using a second sequencing primer, wherein the second sequencing primer comprises a 3' terminal nucleotide which anneals to a second binding site in the at least one nucleic acid template which is more than 5 nt away from the first binding site, wherein the second round of sequencing produces a second sequencing read of the at least one nucleic acid template.

In some embodiments of any of the foregoing methods, the first and/or the second round of sequencing comprises sequencing by synthesis. In some embodiments, the first and/or the second round of sequencing comprises sequencing by ligation. In some embodiments, the coupling comprises conjugating the at least one nucleic acid template to a solid support of the sequencing platform. In some embodiments, the solid support comprises a bead, a well, an array, or a flow cell. In some embodiments, the at least one nucleic acid template comprises an adaptor oligonucleotide ligated to one or both ends of the at least one nucleic acid template. In some embodiments, the first sequencing primer is selectively hybridizable to a primer binding site of the adaptor oligonucleotide. In some embodiments, the second sequencing primer is not selectively hybridizable to the primer binding site of the adaptor oligonucleotide. In some embodiments, the second sequencing read comprises an informative locus. In some embodiments, the informative locus is a polymorphic locus. In some embodiments, the first sequencing read comprises a first informative locus and the second sequencing read comprises a second informative locus. In some embodiments, the method comprises determining that a first allele detected at the first informative locus and a second allele detected at the second informative locus are in phase. In some embodiments, the second sequencing primer is designed to hybridize to a location that is within x nt upstream of the informative locus, wherein x is a number that is less than an average sequencing read length produced by the first or second round of sequencing. In some embodiments, the removing comprises a denaturing step. In some embodiments, the removing further comprises a washing step. In some embodiments, the method further comprises subjecting the at least one nucleic acid template to one or more additional rounds of sequencing, wherein the one or more additional rounds of sequencing comprise the steps of:

(i) removing a previously annealed sequencing primer and previously generated sequencing read from the at least one nucleic acid template; (ii) annealing an additional sequencing primer to the at least one nucleic acid template; and (iii) subjecting the at least one nucleic acid template to an additional round of sequencing using the additional sequencing primer, thereby producing an additional sequencing read of the at least one nucleic acid template. In some embodiments, the additional sequencing primer comprises a 3' terminal nucleotide which hybridizes to a binding site that is more than 5 nt away from a binding site of the 3' terminal nucleotide of the previously annealed sequencing primer. In some embodiments, a first allele detected by the first sequencing read, a second allele detected by the second sequencing read, and an additional allele detected by the additional sequencing read are determined to be in phase. In some embodiments, the additional sequencing primer and the previously annealed sequencing primer are designed to hybridize to genomic locations that map to a single chromosome. In some embodiments, the genomic locations that map to a single chromosome span a distance that is less than a length of the at least one nucleic acid template. In some embodiments, the genomic locations that map to a single chromosome span a distance that is less than three-quarters of the length of the at least one nucleic acid template. In some embodiments, the genomic locations that map to a single chromosome span a distance that is less than two-thirds of the length of the at least one nucleic acid template. In some embodiments, the genomic locations that map to a single chromosome span a distance that is less than one half of the length of the at least one nucleic acid template. In some embodiments, the genomic locations that map to a single chromosome span a distance that is about a sequencing read length of the sequencing platform. In some embodiments, the at least one nucleic acid template is a member of a sequencing library. In some embodiments, the sequencing library is a whole-genome sequencing library. In some embodiments, the sequencing library is a target-enriched sequencing library. In some embodiments, the sequencing library is a directional sequencing library. In some embodiments, the sequencing library is not a directional sequencing library. In some embodiments, the sequencing library comprises nucleic acid fragments of an average length. In some embodiments, the average length is about 50 bases to about 10 kb. In some embodiments, the first, second, and optionally additional sequencing reads comprise sequence information from a plurality of loci. In some embodiments, phasing of alleles detected at the plurality of loci is determined based upon the first, second, and optionally additional sequencing reads. In some embodiments, the at least one nucleic acid template comprises a plurality of nucleic acid templates. In some embodiments, the at least one nucleic acid template comprises at least 10,000 nucleic acid templates. In some embodiments, the at least one nucleic acid template comprises 3 billion nucleic acid templates. In some embodiments, the at least one nucleic acid template is coupled to a unique addressable location of the sequencing platform. In some embodiments, the method comprises compiling sequencing reads from the unique addressable location into one data file. In some embodiments, the method comprises determining phasing of a plurality of alleles detected across two or more unique addressable locations. In some embodiments, the two or more unique addressable locations each comprise two or more detected alleles, wherein the two or more detected alleles of each of the two or more unique addressable locations are determined to be in phase if at least one common detected allele is shared by the two or more unique addressable locations. In some embodiments, step (d) of a method disclosed herein comprises subjecting the at least one nucleic acid template to a second round of sequencing using a mixture of second sequencing primers. In some embodiments, the mixture of second sequencing primers comprises a pair of primers, wherein each primer in the primer pair is designed to sequence a forward or reverse complement strand containing a locus. In some embodiments, primers within the mixture are designed and/or selected to have minimal potential to hybridize to the same nucleic acid template.

In some embodiments of any of the aforementioned methods, the template comprises DNA. In some embodiments, the template comprises RNA. In some embodiments, one or more methods disclosed herein is used to provide phasing information for two or more alleles separated by a distance of over 150 bases, over 300 bases, over 500 bases, over 600 bases, over 700 bases, over 800 bases, over 900 bases, over 1000 bases (1 kb), over 5 kb, over 10 kb, over 50 kb, over 100 kb, over 500 kb, over 1000 kb (1 Mb), over 5 Mb, over 10 Mb, over 50 Mb, over 100 Mb, over 150 Mb, over 200 Mb, over 250 Mb, or over 300 Mb.

Also provided herein is a kit, comprising: (a) one or more oligonucleotide primers for performing a sequencing reaction; and (b) instructions for practicing a method of any of the preceding claims using the one or more oligonucleotide primers.

Also provided herein is a computer readable medium comprising computer executable code that, upon execution by a computer processor, implements a method comprising: (a) accessing a data file in computer memory that comprises a plurality of sequencing reads corresponding to a first addressable location of a sequencing platform, wherein the sequencing reads are generating by subjecting a first nucleic acid template coupled to the addressable location to a first and at least a second round of sequencing, wherein the first and at least second rounds of sequencing are performed using a first and second sequencing primer, respectively; (b) using the data file, detecting a first detected allele at a first locus of the nucleic acid template and detecting a second detected allele at a second locus of the nucleic acid template; and (c) determining the first and second detected allele to be in phase based upon said detecting. In some embodiments, the method further comprises: (d) accessing a second data file in computer memory that comprises a plurality of sequencing reads corresponding to a second addressable location of a sequencing platform, wherein the sequencing reads are generated by subjecting a second nucleic acid template coupled to the addressable location to the first and the at least second round of sequencing; (e) using the second data file, detecting a first detected allele at a first locus of the second nucleic acid template and detecting a second detected allele at a second locus of the second nucleic acid template; and (f) determining the first and second detected alleles of the second nucleic acid template to be in phase with the first and second detected alleles of the first nucleic acid template if the first or second detected allele of the second nucleic acid template is shared in common with the first nucleic acid template.

INCORPORATION BY REFERENCE

All publications, patents, and patent applications mentioned in this specification are herein incorporated by reference to the same extent as if each individual publication,

BRIEF DESCRIPTION OF THE DRAWINGS

The novel features of the invention are set forth with particularity in the appended claims. A better understanding of the features and advantages of the present invention will be obtained by reference to the following description that sets forth illustrative embodiments, in which the principles of the invention are utilized, and the accompanying drawings of which:

DETAILED DESCRIPTION OF THE INVENTION

Figure 1:
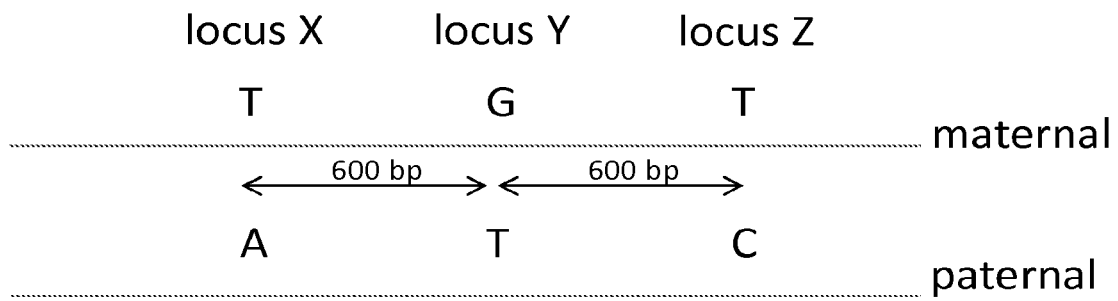
FIG. 1 and FIG. 2 illustrate the current limitations of NGS sequencing in obtaining phasing information for a plurality of alleles.

Throughout this application, various embodiments are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Unless otherwise specified, terms and symbols of genetics, molecular biology, biochemistry and nucleic acid used herein follow those of standard treatises and texts in the field, e.g. Kornberg and Baker, *DNA Replication*, Second Edition (W.H. Freeman, New York, 1992); Lehninger, Biochemistry, Second Edition (Worth Publishers, New York, 1975); Strachan and Read, Human *Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); Sambrook, Fritsch & Maniatis, *Molecular Cloning: A Laboratory Manual*, Fourth Edition (2012); *Oligonucleotide Synthesis* (M. J. Gait, ed., 1984); *Nucleic Acid Hybridization* (B. D Hames & S. J. Higgins, eds., 1984); *A Practical Guide to Molecular Cloning* (B. Perbal, 1984); and a series, *Methods in Enzymology* (Academic Press, Inc.) and the like.

Definitions

As used in the specification and claims, the singular forms "a", "an" and "the" can include plural references unless the context clearly dictates otherwise. For example, the term "a primer" can include a plurality of primers, including mixtures thereof.

The terms "determining", "measuring", "evaluating", "assessing," "assaying," and "analyzing" can be used interchangeably herein to refer to any form of measurement, and include determining if an element is present or not. These terms can include both quantitative and/or qualitative determinations. Assessing may be relative or absolute. "Assessing the presence of" can include determining the amount of something present, as well as determining whether it is present or absent.

As used herein, the term "phasing" can refer to the process of determining whether two or more nucleic acid sequences are located on the same nucleic acid template, the same fragment of a chromosome, or the same chromosome.

As used herein, the term "haplotype" can refer to a haploid genotype, e.g., a combination or set of nucleic acid sequences detected at a plurality of loci which are typically inherited as a unit and are linked, for example during a translocation event. A haplotype can provide a distinctive genetic pattern of an individual. A haplotype can be determined for one locus, several loci, or an entire chromosome depending on the number of recombination events that occur between a given set of loci. The nucleic acid sequences are not limited to any specific type and can include, by way of example only, conserved genetic sequences (e.g., non-variant) or variant genetic sequences (e.g., polymorphisms). For example, single nucleotide polymorphisms (SNPs), short tandem repeats (STRs), including, for example, di-, tri-, and tetra-nucleotide repeats, copy number variations (CNVs), insertions, deletions, inversions, methylations, etc. can be considered variant genetic sequences. Such markers can be found in various publications and databases including, for example, the ATCC short tandem repeat (STR) database, the Human SNP Database, the NCBI dbSNP database, Celera Human SNP database, SNP Database of the Genome Analysis Group, and the like.

The term "phased alleles" can refer to the distribution of the particular alleles on a nucleic acid template, a single chromosomal region, and/or a single chromosome. Accordingly, the "phase" of two alleles can refer to a characterization or determination of whether the alleles are located on a single chromosome or two separate chromosomes (e.g., a maternally or paternally inherited chromosomes). Unless otherwise stated, "haplotype" and "phased alleles" can be considered synonymous.

"Nucleotides" and "nt" can be used interchangeably herein to generally refer to biological molecules that can form nucleic acids. Nucleotides can have moieties that contain not only the known purine and pyrimidine bases, but also other bases that have been modified. Such modifications include acylated purines or pyrimidines, methylated purines or pyrimidines, alkylated riboses, or other heterocycles.

As used herein, the term "oligonucleotide" can refer to a polynucleotide chain, typically less than 200 residues long, most typically between 15 and 100 nucleotides long, but also intended to encompass longer polynucleotide chains. Oligonucleotides can be single- or double-stranded. The terms "oligonucleotide probe" or "probe", as used herein, can refer to an oligonucleotide capable of hybridizing to a complementary nucleotide sequence. As used herein, the term "oligonucleotide" can be used interchangeably with the terms "primer", "adaptor" and "probe".

The term "polynucleotide", "nucleic acid", or grammatical equivalents, can refer to two or more nucleotides covalently linked together. A nucleic acid described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference. Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469, 863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook, all of which are incorporated by reference. Nucleic acids containing one or more carbocyclic sugars are also included within the definition of nucleic acids (see Jenkins et al., Chem. Soc. Rev. (1995) pp 169-176, hereby incorporated by reference). Several nucleic acid analogs are described in Rawls, C & E News Jun. 2, 1997 page 35, hereby incorporated by reference. "Locked nucleic acids" are also included within the definition of nucleic acid analogs. LNAs can be a class of nucleic acid analogues in which the ribose ring is "locked" by a methylene bridge connecting the 2'-O atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some embodiments. The target nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As used herein, the terms "hybridization", "hybridizing" and "annealing" can be used interchangeably and can refer to the pairing of complementary nucleic acids.

The term "primer", as used herein, can refer to an oligonucleotide, generally with a free 3' hydroxyl group, that is capable of hybridizing with a template (such as a target polynucleotide, target DNA, target RNA or a primer extension product) and is also capable of promoting polymerization of a polynucleotide complementary to the template. A primer can contain a non-hybridizing sequence that constitutes a tail of the primer. A primer can still hybridize to a target even though its sequences are not fully complementary to the target.

"Complementary", as used herein, can refer to complementarity to all or only to a portion of a sequence. The number of nucleotides in the hybridizable sequence of a specific oligonucleotide primer can be such that stringency conditions used to hybridize the oligonucleotide primer can prevent excessive random non-specific hybridization. The number of nucleotides in the hybridizing portion of the oligonucleotide primer can be at least as great as the defined sequence on the target polynucleotide that the oligonucleotide primer hybridizes to, namely, at least 5, at least 6, at least 7, at least 8, at least 9, at least 10, at least 11, at least 12, at least 13, at least 14, at least 15, at least about 20, or from about 6 to about 10 or 6 to about 12, or 12 to about 200 nucleotides, or about 10 to about 50 nucleotides. In general, the target polynucleotide can be larger than the oligonucleotide primer or primers as described previously.

The term "genomic sequence", as used herein, can refer to a sequence that occurs in a genome. RNAs can be transcribed from a genome; this term can encompass sequence that exist in the nuclear genome of an organism, as well as sequences that are present in a cDNA copy of an RNA (e.g., an mRNA) transcribed from such a genome.

The term "target polynucleotide,", "target region", or "target", as used herein, can refer to a polynucleotide of interest under study. A target polynucleotide can contain one or more sequences or loci that are of interest and under study. A target polynucleotide can comprise, for example, a genomic region. The genomic region can comprise all or a portion of a chromosome.

The genomic region can comprise a plurality of loci. The genomic region can comprise a plurality of loci for which phasing and/or haplotype information is desired.

The terms "template", "template strand", "template DNA" and "template nucleic acid" can be used interchangeably herein to refer to a strand of nucleic acid (e.g., DNA) that is copied by an amplification cycle.

The term "mutation", as used herein, can refer to a change of the nucleotide sequence of a genome. Mutations can involve large regions of a genome (e.g., copy number variation). Mutations can involve small regions of a genome. Examples of mutations involving small sections of a genome include, e.g., point mutations or single nucleotide polymorphisms, multiple nucleotide polymorphisms, insertions (e.g., insertion of one or more nucleotides at a locus), multiple nucleotide changes, deletions (e.g., deletion of one or more nucleotides at a locus), and inversions (e.g., reversal of a sequence of one or more nucleotides).

The term "locus", as used herein, can refer to a location of a gene, a nucleotide, or a sequence on a chromosome and/or in a genome. A locus can be considered "polymorphic" or to have a "polymorphism" if there exists in a population two or more forms of a nucleotide or sequence at the locus (e.g., if the locus comprises variant genetic sequences). An "allele" of a locus, as used herein, can refer to an alternative form of a nucleotide or sequence at the locus. A "wild-type allele" can refer to an allele that has the highest frequency in a population of subjects. A "mutant allele" can refer to an allele that has a lower frequency that a "wild-type allele". An "informative" locus, as used herein, can refer to a locus which can be used to determine phasing information of two or more alleles. The informative locus can be a polymorphic locus.

The term "single nucleotide polymorphism", or "SNP", as used herein, can refer to a type of genomic sequence variation resulting from a single nucleotide substitution within a sequence. "SNP alleles" or "alleles of a SNP" can refer to alternative forms of the SNP at a given locus.

The term "genotyping", as used herein, can refer to a process of determining differences in the genetic make-up (genotype) of an individual, e.g., by examining the individual's DNA sequence using a biological assay. The biological assay can comprise a sequencing reaction.

As used herein, a "sample" or "nucleic acid sample" can refer to any substance containing or presumed to contain nucleic acid. The sample can be a biological sample obtained from a subject.

An "addressable location", as used herein, can refer to a location that can be recorded and/or tracked throughout any of the procedures carried out during one or more methods described herein.

Overview

Provided herein are methods, compositions, and kits useful for sequence analysis of nucleic acids. The subject methods, compositions, and kits can be useful for obtaining accurate phasing and/or haplotyping information using NGS technologies. For example, the methods, compositions, and kits provided herein can be used to determine phasing of a plurality of alleles that are separated by a distance that is greater than a distance of an NGS sequence read or paired read. The methods and kits provided herein can be used to obtain phasing information for detected alleles that map to two or more loci. For example, the methods and kits provided herein can be used for determining whether detected alleles that map to two or more loci are located on the same nucleic acid template, on the same chromosome or chromosome region, or on different chromosomes or chromosomal regions in a chromosome pair. The methods and kits can be used to determine a plurality of polymorphic markers at a plurality of loci within a nucleic acid template. The methods and kits described herein can also be used to obtain phasing information for a plurality of alleles that are detected on different nucleic acid templates. One or more phasing methods disclosed herein can be used to provide phasing information for two or more alleles. The two or more alleles may be separated by a distance of over 150 bases, over 300 bases, over 500 bases, over 600 bases, over 700 bases, over 800 bases, over 900 bases, over 1000 bases (1 kb), over 5 kb, over 10 kb, over 50 kb, over 100 kb, over 500 kb, over 1000 kb (1 Mb), over 5 Mb, over 10 Mb, over 50 Mb, over 100 Mb, over 150 Mb, over 200 Mb, over 250 Mb, or over 300 Mb.

The methods and kits described herein can also be used to differentiate between closely related nucleic acid sequences, e.g., to distinguish a gene from a closely related pseudogene. Such methods can be useful, for example, for haplotyping, SNP phasing, determining downstream exons in RNA-seq, and in genetic diagnostics applications. The methods, kits and compositions described herein can utilize sequential sequencing of a nucleic acid template. Altogether, the phasing methods disclosed herein provide an improvement over the existing methods by offering a highly parallel, efficient method for obtaining phasing information.

Figure 2:
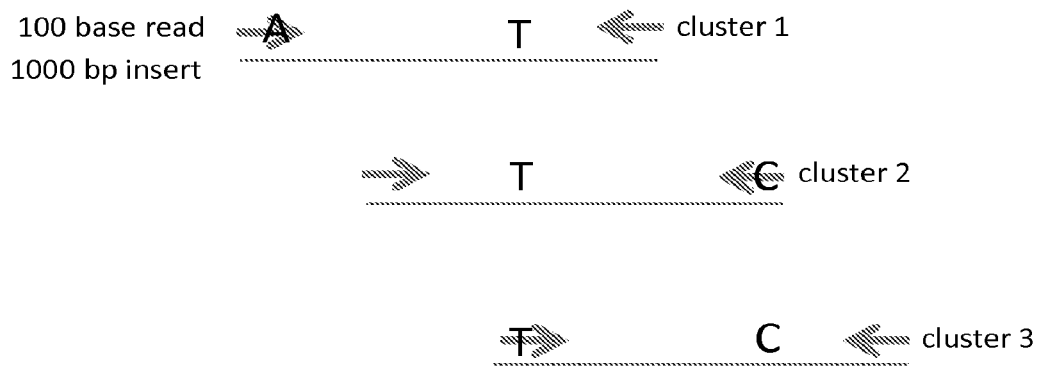

FIG. 1 and FIG. 2 illustrate current limitations of NGS sequencing in obtaining phasing information for a plurality of alleles. FIG. 1 depicts a chromosome pair comprising a maternal and paternal chromosome obtained from genomic DNA from a subject. The chromosomes comprise a plurality of loci: locus X, locus Y, which is located, e.g., 600 bp downstream of locus X, and locus Z, which is located, e.g., 600 bp downstream of locus Y. The maternal chromosome comprises the following alleles: allele T at locus X ($X_T$, allele G at locus Y ($Y_G$), and allele T at locus Z ($Z_T$). By contrast, the paternal chromosome comprises the following alleles, allele A at locus X ($X_A$), allele T at locus Y ($Y_T$), and allele C at locus Z ($Z_C$). FIG. 2 depicts a current embodiment NGS sequencing method which is unable to determine phasing of alleles at loci X, Y, and Z. Genomic DNA from the subject is fragmented into ~1000 bp DNA fragments. The fragments are spatially separated and clonally amplified into clusters. By way of example only, clusters 1-3 tile overlapping regions which span loci X, Y, and Z. The clusters then undergo next generation sequencing, e.g., on an Illumina platform. Next generation sequencing typically produces sequencing reads from one or both ends of the DNA fragments, due to the sequencing adaptors attached to one or both ends of the fragments, wherein the sequencing adaptors comprise sequencing primer binding sites (not shown in the figure). The sequencing reads can have read lengths of, e.g., 100 nt, so the next generation sequencing in this example does not provide sequencing information across the entire template molecule. In this particular example, paired end sequencing is employed, producing sequencing reads from both ends of the template DNA fragments, each read having a read length of 100 nt (as depicted by thick gray arrows in FIG. 2). Accordingly, the DNA template fragment of cluster 1 comprises $X_A$ and $Y_T$, however, only $X_A$ is detected by the sequencing reads. The DNA template fragment of cluster 2 comprises $Y_T$ and $Z_C$, however, only $Z_C$ is detected by the sequencing reads. The DNA template fragment of cluster 3 comprises $Y_T$ and $Z_C$, however, only $Y_T$ is detected by the sequencing reads. Because sequencing reads from clusters 1-3 only detect a single allele at a single locus for each cluster, phasing information is not generated for the detected alleles $X_A$, $Y_T$, and $Z_C$, e.g., whether they are located on the same template molecule, the same chromosomal region, or the same chromosome.

Figure 3:
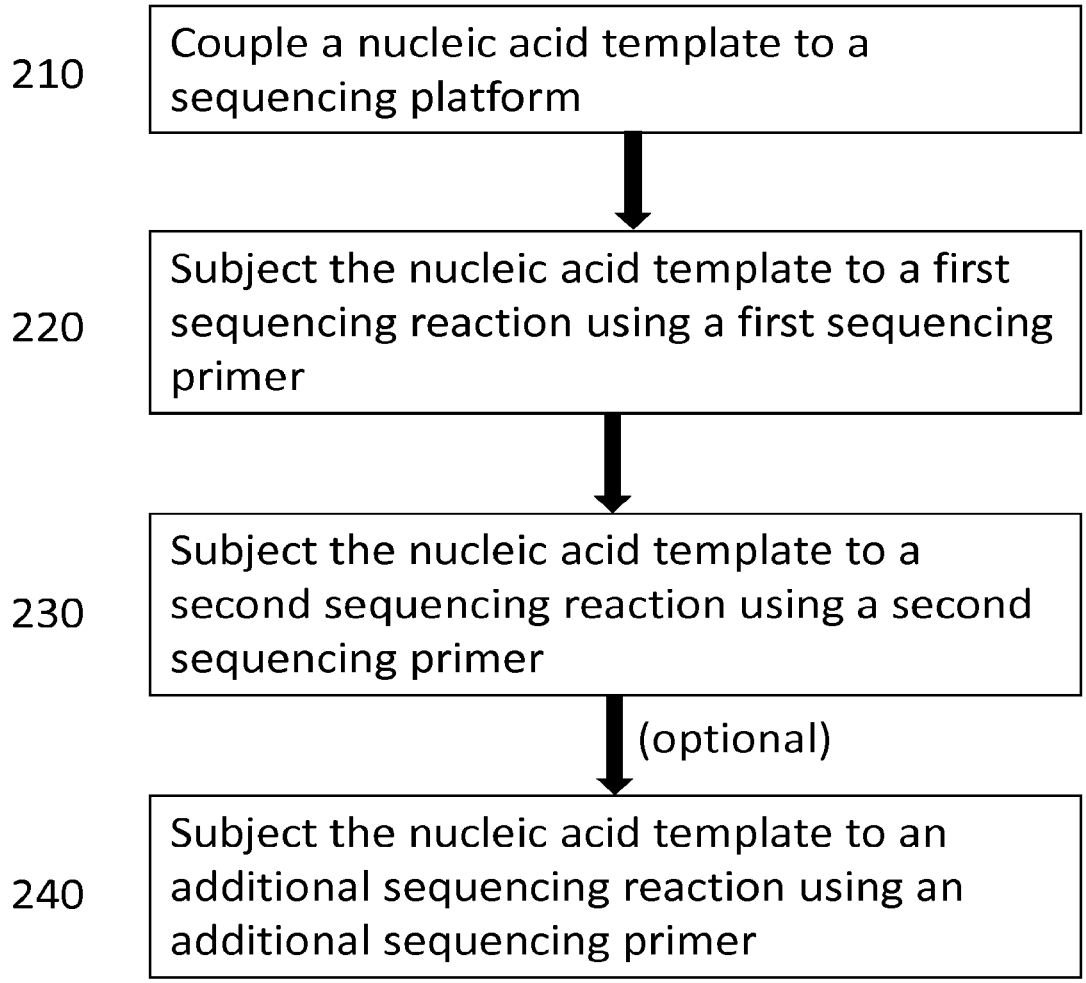
FIG. 3 depicts an exemplary workflow of a method described herein.

FIG. 3 depicts an exemplary workflow of a phasing method described herein. The method can comprise a first step 210 of coupling a nucleic acid template to a sequencing platform. The coupling can comprise attaching the nucleic acid template to a solid support of the sequencing platform. Coupling can in some cases include formation of a covalent bond (e.g., formed by ligation), or a noncovalent bond (e.g., formed by hybridization) between the template and the solid support of the sequencing platform. In some cases, coupling does not involve formation of a covalent bond or noncovalent bond between the template and the solid support of the sequencing platform. In some cases, coupling can include associating two entities, e.g., placing an entity, such as a nucleic acid template, in a well. In some cases, the nucleic acid template is coupled to a unique addressable location of the sequencing platform. For example, a plurality of nucleic acid templates can be coupled to a sequencing platform, wherein each of the plurality of templates is coupled to a unique addressable location of the sequencing platform.

Coupling of nucleic acid templates to unique addressable locations of a sequencing platform can comprise attaching the templates to the unique addressable locations and/or can comprise confining the templates within the unique addressable locations (e.g., confining to a well). For example, a template can be attached to a solid support (e.g., a bead) and the solid support confined within the unique addressable location, such as, e.g., depositing the bead in a well. The method can further comprise a second step 220 of subjecting the nucleic acid template to a first sequencing reaction using a first sequencing primer. The first sequencing primer can initiate sequencing at a first location on the nucleic acid template. The first sequencing reaction can generate a first sequencing read. The first sequencing read can provide the sequence of a first region of the nucleic acid template. The method can further comprise a second step 230 of subjecting the nucleic acid template to a second sequencing reaction using a second sequencing primer. The second sequencing primer can initiate sequencing at a second location on the nucleic acid template. The second location can be distinct from the first location. In some cases, a 3' terminal nucleotide of the second primer can hybridize to a location that is more than 5 nt away from a binding site of a 3' terminal nucleotide of the first primer. The second sequencing reaction can generate a second sequencing read. The second sequencing read can provide the sequence of a second region of the nucleic acid template which is distinct from the first region of the nucleic acid template. In some embodiments, the nucleic acid template is optionally subjected to one or more additional rounds of sequencing (depicted as step 240) using additional sequencing primers.

Nucleic acid templates can be subjected to any number of rounds of sequencing as described herein. For example, nucleic acid templates can be subjected to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10000, 100000, or more than 100000 rounds of sequencing according to one or more phasing methods described herein. Nucleic acid templates can be subjected to about 2 to about 8 rounds of sequencing, about 6 to about 20 rounds of sequencing, about 10 to about 100 rounds of sequencing, about 50 to about 500 rounds of sequencing, about 100 to about 1000 rounds of sequencing, about 500 to about 2000 rounds of sequencing, about 1000 to about 10000 rounds of sequencing, or more than about 10000 rounds of sequencing according to one or more phasing methods described herein.

The rounds of sequencing can produce any number of sequencing reads for the nucleic acid template. For example, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10000, 100000, or more than 100000 sequencing reads can be generated for any given nucleic acid template. About 1 to about 8 sequencing reads, about 6 to about 20 sequencing reads, about 10 to about 100 sequencing reads, about 50 to about 500 sequencing reads, about 100 to about 1000 sequencing reads, about 500 to about 2000 sequencing reads, about 1000 to about 10000 sequencing reads, or more than about 10000 sequencing reads can be generated for any given nucleic acid template.

In some embodiments, the first, second, and/or any additional rounds of sequencing are conducted using a plurality of primers. For example, any round of sequencing designed to sequence a particular locus can comprise use of a pair of primers, wherein each primer in the primer pair is designed to sequence a forward or reverse complement strand containing the locus. For example, any round of sequencing can comprise sequencing using a mixture of primers. Primers within a mixture can be designed and/or selected to have minimal potential to hybridize to the same nucleic acid template. For example, primers within a mixture can be designed to hybridize to locations that are at least 1 kb, 2 kb, 3 kb, 4 kb, 5 kb, 10 kb, 20 kb, 30 kb, 40 kb, 50 kb, 60 kb, 70 kb, 80 kb, 90 kb, 100 kb, 200 kb, 300 kb, 400 kb, 500 kb, 600 kb, 700 kb, 800 kb, 900 kb, 1000 kb (1 Mb), 2 Mb, 3 Mb, 4 Mb, 5 Mb, 6 Mb, 7 Mb, 8 Mb, 9 Mb, 10 Mb, 20 Mb, 30 Mb, 40 Mb, 50 Mb, 60 Mb, 70 Mb, 80 Mb, 90 Mb, 100 Mb, or 200 Mb apart. Primers within a mixture can be designed to hybridize to different chromosomes. A mixture of primers used for any round of sequencing can comprise any number of primers, for example, can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10000, 100000, or more than 100000 primers. A mixture of primers used for any round of sequencing can comprise about 1 to about 8 primers, about 6 to about 20 primers, about 10 to about 100 primers, about 50 to about 500 primers, about 100 to about 1000 primers, about 500 to about 2000 primers, about 1000 to about 10000 primers, or more than about 10000 primers.

In some cases, the first, second, and optionally additional sequencing reads can be compiled to produce sequence information for the nucleic acid template. For example, first, second, and optionally additional sequencing reads from a unique addressable location can be compiled to produce sequence information for the nucleic acid template coupled to that unique addressable location.

Figure 4:
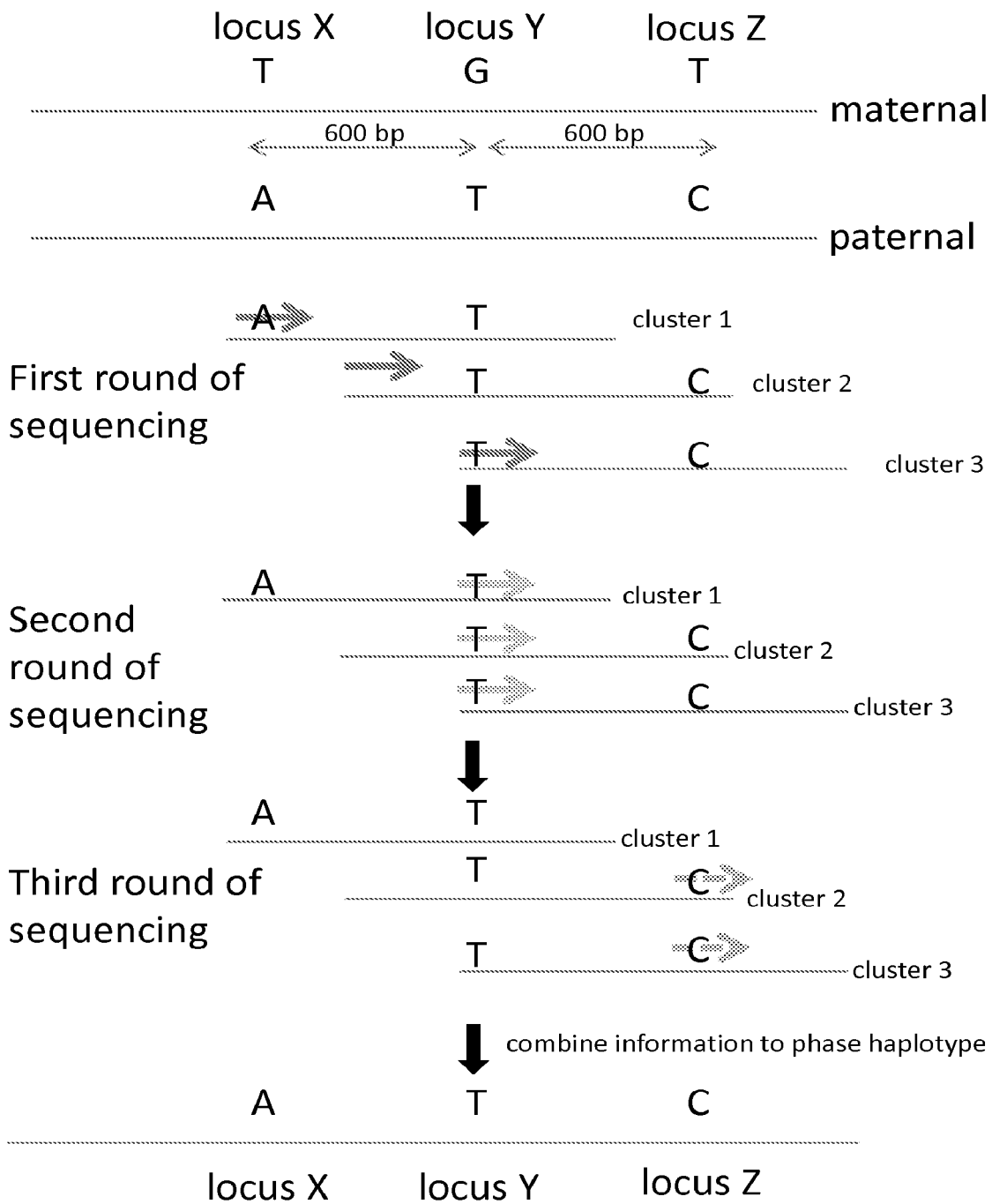
FIG. 4 depicts an exemplary embodiment of a method described herein.

FIG. 4 depicts an exemplary embodiment of a phasing method described herein, and highlights advantages of the subject method for obtaining phasing information for a plurality of alleles. FIG. 4 depicts the same chromosome pair comprising a maternal and paternal chromosome obtained from genomic DNA from a subject as depicted in FIG. 1 and FIG. 2. As in FIG. 1 and FIG. 2, the chromosomes comprise a plurality of loci: locus X, locus Y, which is located, e.g., 600 bp downstream of locus X, and locus Z, which is located, e.g., 600 bp downstream of locus Y. As in FIG. 1 and FIG. 2, the maternal chromosome comprises the following alleles: allele T at locus X ($X_T$), allele G at locus Y ($Y_G$), and allele T at locus Z ($Z_T$). As in FIG. 1 and FIG. 2, the paternal chromosome comprises the following alleles, allele A at locus X ($X_A$), allele T at locus Y ($Y_T$), and allele C at locus Z ($Z_C$). As in FIG. 1 and FIG. 2, genomic DNA from the subject is fragmented into ~1000 bp DNA fragments. As in FIG. 1 and FIG. 2, the fragments are spatially separated and clonally amplified into clusters. As in FIG. 1 and FIG. 2, clusters 1-3 tile overlapping regions which span loci X, Y, and Z. The clusters are then subjected to sequential rounds of sequencing according to a phasing method described herein. A first round of sequencing is performed using a first sequencing primer. The first sequencing primer can be designed to selectively hybridize to a sequencing primer binding site of a sequencing adaptor attached to a first end of the cluster templates. The first round of sequencing using the first sequencing primer provides a first set of sequencing reads (dark gray arrows) of a first end of the cluster templates. Because locus X happens to be located near the end of the first end of cluster 1, Allele $A_A$ is detected by the first read of cluster 1. The extension strands resulting from extension of the first sequencing primer are then denatured and removed from the clusters. In a next step, a second round of sequencing is performed using a second sequencing primer. The second sequencing primer can be designed to hybridize to a genomic location upstream of locus Y and to sequence locus Y. Accordingly, the second round of sequencing produces a second set of sequencing reads (medium gray arrows). Because clusters 1, 2, and 3 comprise locus Y, the second set of sequencing reads comprise reads from clusters 1, 2, and 3. The second set of sequencing reads detect allele T at locus Y ($Y_T$) in clusters 1, 2, and 3. The extension strands resulting from extension of the second sequencing primer are then denatured and removed from the clusters. In a next step, a third round of sequencing is performed using a third sequencing primer. The third sequencing primer can be designed to hybridize to a genomic location upstream of locus Z and to sequence locus Z. Accordingly, the third round of sequencing produces a third set of sequencing reads (stippled medium gray arrows). Because clusters 2 and 3, but not cluster 1, comprise locus Z, the third set of sequencing reads comprise reads from clusters 2 and 3 but not from cluster 1. The third set of sequencing reads detect allele C at locus Z ($Z_C$) in clusters 2 and 3. Sequence data from the first, second, and third sets of sequencing reads is compiled and used to determine phasing of the detected alleles at loci X, Y, and Z. Because the first and second set of sequencing reads reveal $X_A$ and $Y_T$ in cluster 1, it can be determined that $X_A$ and $Y_T$ are in phase (e.g., on the same nucleic acid fragment). Because the second and third sets of sequencing reads reveal $Y_T$ and $Z_C$ in clusters 2 and 3, it can be determined that $Y_T$ and $Z_C$ are in phase (e.g., on the same nucleic acid fragment). Moreover, because the first, second, and third clusters share a common allele ($Y_T$), it can be determined that $X_A$, $Y_T$, and $Z_C$ are all in phase. Because $X_A$, $Y_T$, and $Z_C$ are all in phase, a haplotype of the subject can be determined to be $X_A Y_T Z_C$.

Figure 5:
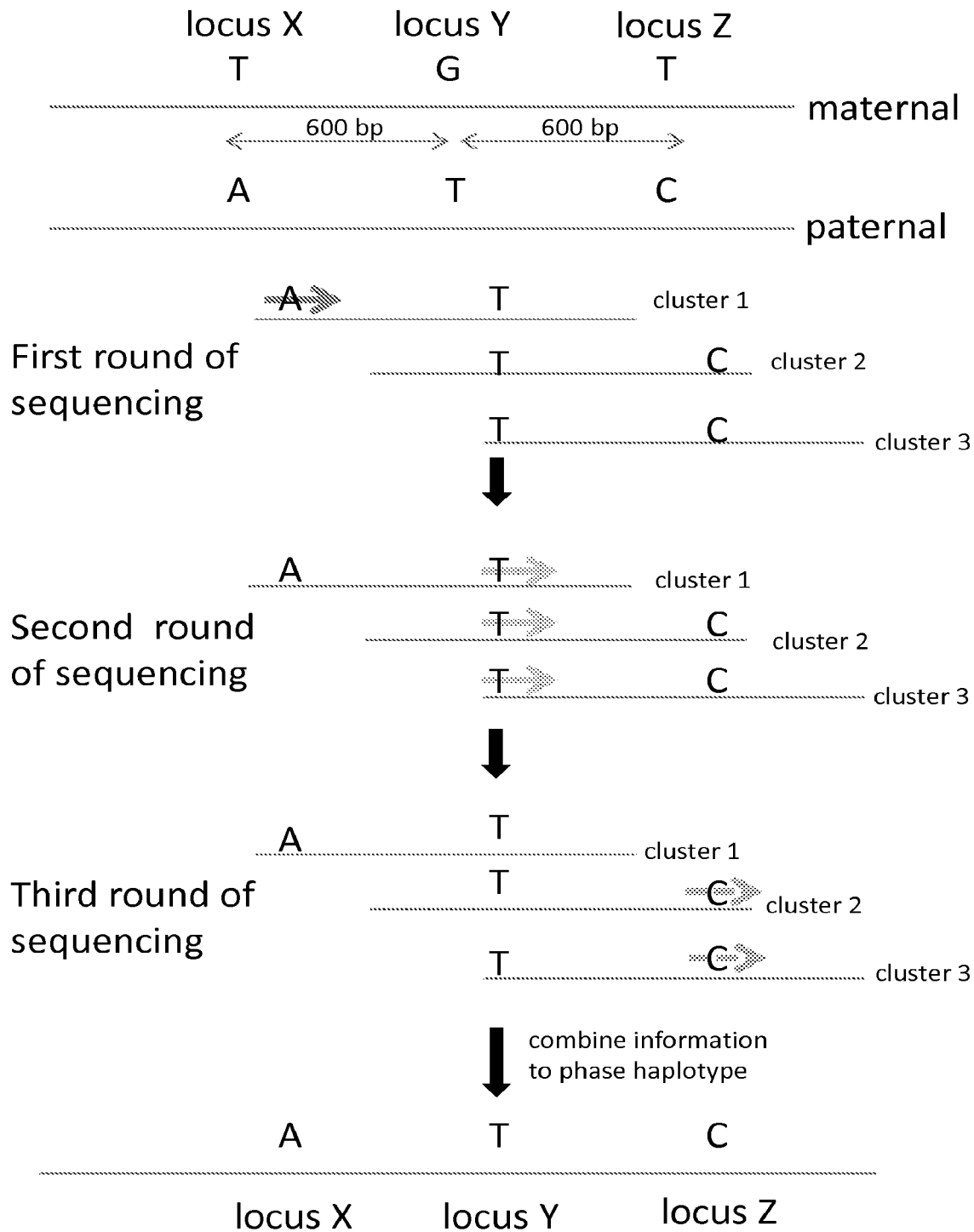
FIG. 5 depicts another exemplary embodiment of a method described herein.

FIG. 5 depicts another exemplary embodiment of a phasing method described herein. FIG. 5 depicts the same chromosome pair comprising a maternal and paternal chromosome obtained from genomic DNA from a subject as depicted in FIG. 1 and FIG. 2. As in FIG. 1 and FIG. 2, the chromosomes comprise a plurality of loci: locus X, locus Y, which is located, e.g., 600 bp downstream of locus X, and locus Z, which is located, e.g., 600 bp downstream of locus Y. As in FIG. 1 and FIG. 2, the maternal chromosome comprises the following alleles: allele T at locus X ($X_T$), allele G at locus Y ($Y_G$), and allele T at locus Z ($Z_T$). As in FIG. 1 and FIG. 2, the paternal chromosome comprises the following alleles, allele A at locus X ($X_A$), allele T at locus Y ($Y_T$), and allele C at locus Z ($Z_C$). As in FIG. 1 and FIG. 2, genomic DNA from the subject is fragmented into ~1000 bp DNA fragments. As in FIG. 1 and FIG. 2, the fragments are spatially separated and clonally amplified into clusters. As in FIG. 1 and FIG. 2, clusters 1-3 tile overlapping regions which span loci X, Y, and Z. The clusters are then subjected to sequential rounds of sequencing according to a phasing method described herein. A first round of sequencing is performed using a first sequencing primer. The first sequencing primer can be designed to selectively hybridize to a genomic location upstream of locus X and to sequence locus X. The first round of sequencing produces a first set of sequencing reads. Because cluster 1, but not clusters 2 or 3, comprise locus X, the first set of sequencing reads comprises a read from cluster 1 but not from clusters 2 or 3. The first set of sequencing reads detects allele A at locus X($X_A$). The extension strands resulting from extension of the first sequencing primer are then denatured and removed from the clusters. In a next step, a second round of sequencing is performed using a second sequencing primer. The second sequencing primer can be designed to hybridize to a genomic location upstream of locus Y and to sequence locus Y. Accordingly, the second round of sequencing produces a second set of sequencing reads (medium gray arrows). Because clusters 1, 2, and 3 all comprise locus Y, the second set of sequencing reads comprise reads from clusters 1, 2, and 3. The second set of sequencing reads detect allele T at locus Y (($Y_T$) in clusters 1, 2, and 3. The extension strands resulting from extension of the second sequencing primer are then denatured and removed from the clusters. In a next step, a third round of sequencing is performed using a third sequencing primer. The third sequencing primer can be designed to hybridize to a genomic location upstream of locus Z and to sequence locus Z. Accordingly, the third round of sequencing produces a third set of sequencing reads (stippled medium gray arrows). Because clusters 2 and 3, but not cluster 1, comprise locus Z, the third set of sequencing reads comprise reads from clusters 2 and 3 but not from cluster 1. The third set of sequencing reads detect allele C at locus Z ($Z_C$) in clusters 2 and 3. Sequence data from the first, second, and third sets of sequencing reads is compiled and used to determine phasing of the detected alleles at loci X, Y, and Z. Because the first and second set of sequencing reads reveal $X_A$ and $Y_T$ in cluster 1, it can be determined that $X_A$ and $Y_T$ are in phase. Because the second and third sets of sequencing reads reveal $Y_T$ and $Z_C$ in clusters 2 and 3, it can be determined that $Y_T$ and $Z_C$ are in phase. Moreover, because the first, second, and third clusters share a common allele ($Y_T$), it can be determined that $X_A$, $Y_T$, and $Z_C$ are all in phase. Because $X_A$, $Y_T$, and $Z_C$ are all in phase, a haplotype of the subject can be determined to be $X_A Y_T Z_C$.

Reference will now be made in detail to exemplary embodiments. While the disclosed methods and compositions will be described in conjunction with the exemplary embodiments, it will be understood that these exemplary embodiments are not intended to limit the methods and compositions described herein, but can encompass alternatives, modifications and equivalents, which may be included in the spirit and scope described herein Exemplary Nucleic Acid Templates Nucleic acid templates to be sequenced by a method provided herein can comprise DNA. The DNA can be complex DNA, for example genomic DNA. The DNA can be from a linear or circular genome. The DNA can be plasmid DNA, cosmid DNA, bacterial artificial chromosome (BAC), or yeast artificial chromosome (YAC). The DNA can be from more than one individual or organism. The DNA can be double stranded or single stranded. The input DNA can be part of chromatin. The DNA can be associated with histones. The DNA can comprise one or more chromosomes. For example, if the DNA is from a human, the DNA can comprise one or more of chromosome 1, 2, 3, 4, 5, 6, 7, 8, 9, 10, 11, 12, 13, 14, 15, 16, 17, 18, 19, 20, 21, 22, X, or Y. The DNA can be mitochondrial DNA. The DNA can be cell-free DNA. The DNA can be cDNA. The cDNA can be generated from RNA, e.g., mRNA. Nucleic acid templates to be sequenced by a method provided herein can comprise RNA.

Nucleic acid templates to be sequenced by a method provided herein can be obtained from and/or can be in a nucleic acid sample. The nucleic acid sample can be obtained from a subject. A subject can be any biological entity of interest from which phasing and/or haplotype information is desired. The subject can be an animal, plant, fungus, insect, bacteria, algae, virus, cell, tissue, and the like. The animal can be human, non-human primate, dog, cat, cow, pig, sheep, guinea pig, hamster, bird, frog, fish, rat, mouse, other rodent or other animal. A nucleic acid sample can also comprise a mixture of genomes of different species such as host-pathogen, bacterial populations, viral populations, and the like. For example, a DNA sample can comprise DNA (e.g., cDNA) made from a mixture of genomes of different species. Alternatively, the nucleic acid sample can be from a synthetic source.

The nucleic acid sample can be obtained from a biological sample from the subject. The biological sample can be, e.g., a liquid sample, a solid sample, or a combination thereof. Exemplary liquid samples include, but are not limited to ascites, buccal sample, cavity rinse, cerebrospinal fluid, whole blood, plasma, serum, sweat, tears, sputum, saliva, urine, or organ rinse. The sample can be a cell-free sample. Exemplary cell-free samples include, but are not limited to plasma, serum, plasma, urine, sweat, saliva, sputum, and tears. Exemplary solid biological samples include, e.g., tissue biopsy, feces, and the like. A biological sample can also comprise cultured cells or constituents of culture cells (including, e.g., conditioned medium resulting from the growth of cells in cell culture medium, recombinant cells and cell components). The sample can be a single cell. Nucleic acid samples can be obtained from biological samples by any means known to those of skill in the art. For example, nucleic acid can be extracted from a biological sample using liquid extraction (e.g, Trizol, DNAzol) techniques. Nucleic acid can also be extracted using commercially available kits. Nucleic acids can be concentrated by, e.g., centrifugation and/or precipitation. Nucleic acids can be purified by binding to a selective membrane and then by elution. In some cases, gentle handling steps may be taken to avoid shearing of chromosomal or intact DNA during the extraction process. Exemplary gentle handling strategies can include, e.g., pipetting with a wide-bore pipette tip and avoidance of vigorous pipetting and/or vortexing. In some cases, gentle handling steps are unnecessary for preparation of nucleic acid samples.

The nucleic acid sample can be fragmented by any means known in the art or otherwise described herein. The nucleic acids can be fragmented to result in a population of nucleic acid fragments of a desired length. The nucleic acid fragments can be double stranded or single stranded fragments. The length of the nucleic acid fragments can be any length. A nucleic acid fragment to be sequenced by a method described herein can have a length that is less than 300 Mb, less than 200 Mb, less than 100 Mb, less than 50 Mb, less than 40 Mb, less than 30 Mb, less than 20 Mb, less than 10 Mb, less than 5 Mb, less than 3 Mb, less than 2 Mb, less than 1 Mb (1000 kb), less than 900 kb, less than 800 kb, less than 700 kb, less than 600 kb, less than 500 kb, less than 400 kb, less than 300 kb, less than 200 kb, less than 100 kb (100,000 bases), less than 100,000 bases, less than 90,000 bases, less than 80,000 bases, less than 70,000 bases, less than 60,000 bases, less than 50,000 bases, less than 40000 bases, less than 30,000 bases, less than 20,000 bases, less than 10,000 bases, less than 9000 bases, less than 8000 bases, less than 7000 bases, less than 6000 bases, less than 5000 bases, less than 4000 bases, less than 3000 bases, less than 2000 bases, less than 1500 bases, less than 1400 bases, less than 1300 bases, less than 1200 bases, less than 1100 bases, less than 1000 bases, less than 900 bases, less than 800 bases, less than 700 bases, less than 600 bases, less than 500 bases, less than 400 bases, less than 300 bases, less than 250 bases, less than 200 bases, less than 150 bases, less than 100 bases, less than 50 bases, less than 40 bases, less than 30 bases, less than 20 bases, or less than 10 bases. In some cases, a nucleic acid fragment to be sequenced by a method described herein has a length that is about 10 bases, about 20 bases, about 30 bases, about 40 bases, about 50 bases, about 100 bases, about 150 bases, about 200 bases, about 250 bases, about 300 bases, about 400 bases, about 500 bases, about 600 bases, about 700 bases, about 800 bases, about 900 bases, about 1000 bases, about 1100 bases, about 1200 bases, about 1300 bases, about 1400 bases, about 1500 bases, about 1600 bases, about 1700 bases, about 1800 bases, about 1900 bases, about 2000 bases, about 3000 bases, about 4000 bases, about 5000 bases, about 6000 bases, about 7000 bases, about 8000 bases, about 9000 bases, about 10000 bases, about 20000 bases, about 30000 bases, about 40000 bases, about 50000 bases, about 60000 bases, about 70000 bases, about 80000 bases, about 90000 bases, about 100000 bases (100 kb), about 200 kb, about 300 kb, about 400 kb, about 500 kb, about 600 kb, about 700 kb, about 800 kb, about 900 kb, about 1000 kb (1 Mb), about 2 Mb, about 3 Mb, about 5 Mb, about 10 Mb, about 10 Mb, about 30 Mb, about 40 Mb, about 50 Mb, about 100 Mb, about 200 Mb, or about 300 Mb. In some cases, a nucleic acid fragment to be sequenced by a method described herein has a length that is more than about 10 bases, more than about 20 bases, more than about 30 bases, more than about 40 bases, more than about 50 bases, more than about 100 bases, more than about 150 bases, more than about 200 bases, more than about 250 bases, more than about 300 bases, more than about 400 bases, more than about 500 bases, more than about 600 bases, more than about 700 bases, more than about 800 bases, more than about 900 bases, more than about 1000 bases, more than about 1100 bases, more than about 1200 bases, more than about 1300 bases, more than about 1400 bases, more than about 1500 bases, more than about 1600 bases, more than about 1700 bases, more than about 1800 bases, more than about 1900 bases, more than about 2000 bases, more than about 3000 bases, more than about 4000 bases, more than about 5000 bases, more than about 6000 bases, more than about 7000 bases, more than about 8000 bases, more than about 9000 bases, more than about 10000 bases, more than about 20000 bases, more than about 30000 bases, more than about 40000 bases, more than about 50000 bases, more than about 60000 bases, more than about 70000 bases, more than about 80000 bases, more than about 90000 bases, more than about 100000 bases (100 kb), more than about 200 kb, more than about 300 kb, more than about 400 kb, more than about 500 kb, more than about 600 kb, more than about 700 kb, more than about 800 kb, more than about 900 kb, more than about 1000 kb (1 Mb), more than about 2 Mb, more than about 3 Mb, more than about 5 Mb, more than about 10 Mb, more than about 10 Mb, more than about 30 Mb, more than about 40 Mb, more than about 50 Mb, more than about 100 Mb, more than about 200 Mb, or more than about 300 Mb. A nucleic acid fragment to be sequenced by a method described herein can have a length that is between about 10 to about 100 bases, about 50 to about 200 bases, about 100 to about 250 bases, about 150 to about 500 bases, about 300 to about 700 bases, about 400 to about 800 bases, about 600 to about 900 bases, about 800 to about 1000 bases, about 200 to about 1000 bases, about 500 bases to about 10000 bases, or about 2000 bases to about 100000 bases. In some embodiments, the nucleic acid fragment has a length that is over 9000 bases. For example, the nucleic acid fragments can be about 0.9 to about 2 kb, about 1.5 to about 4 kb, about 2 to about 6 kb, about 5 to about 8 kb, or about 7 to about 10 kb, about 10 to about 100 kb, about 50 kb to about 1 Mb, about 1 Mb to about 50 Mb, about 10 Mb to about 300 Mb. One of skill in the art will readily understand that the length of the nucleic acid templates to be sequenced by a method disclosed herein can be any length. Length of nucleic acid templates to be sequenced by a method disclosed herein can vary depending on the sequencing platform used in practicing a method disclosed herein. In some embodiments, the nucleic acid sample is not fragmented.

The nucleic acid sample can be enriched for target polynucleotides of interest. Target polynucleotides can comprise polynucleotides that map to genomic regions of interest. A genomic region of interest can be any genomic region from which phasing and/or haplotype information is desired. The genomic region of interest can comprise a region of a chromosome. The genomic region of interest can comprise a whole chromosome. The chromosome can be a diploid chromosome. In a human genome, for example, the diploid chromosome can be any of chromosomes 1, 2, 3, 4, 5, 6, 7, 8, 9, 10, 11, 12, 13, 14, 15, 16, 17, 18, 19, 20, 21, 22, 23. In some cases, the chromosome can be an X or Y chromosome. In some cases, the genomic region of interest comprises a portion of a chromosome. A genomic region of interest can be of any length. The genomic region of interest can have a length that is between, e.g., about 1 to about 10 bases, about 5 to about 50 bases, about 10 to about 100 bases, about 70 to about 300 bases, about 200 bases to about 1000 bases (1 kb), about 700 bases to about 2000 bases, about 1 kb to about 10 kb, about 5 kb to about 50 kb, about 20 kb to about 100 kb, about 50 kb to about 500 kb, about 100 kb to about 2000 kb (2 Mb), about 1 Mb to about 50 Mb, about 10 Mb to about 100 Mb, about 50 Mb to about 300 Mb. For example, a genomic region of interest can be over 1 base, over 10 bases, over 20 bases, over 50 bases, over 100 bases, over 200 bases, over 400 bases, over 600 bases, over 800 bases, over 1000 bases (1 kb), over 1.5 kb, over 2 kb, over 3 kb, over 4 kb, over 5 kb, over 10 kb, over 20 kb, over 30 kb, over 40 kb, over 50 kb, over 60 kb, over 70 kb, over 80 kb, over 90 kb, over 100 kb, over 200 kb, over 300 kb, over 400 kb, over 500 kb, over 600 kb, over 700 kb, over 800 kb, over 900 kb, over 1000 kb (1 Mb), over 2 Mb, over 3 Mb, over 4 Mb, over 5 Mb, over 6 Mb, over 7 Mb, over 8 Mb, over 9 Mb, over 10 Mb, over 20 Mb, over 30 Mb, over 40 Mb, over 50 Mb, over 60 Mb, over 70 Mb, over 80 Mb, over 90 Mb, over 100 Mb, or over 200 Mb.

A genomic region of interest can comprise one or more informative loci. An informative locus can be a polymorphic locus, e.g., comprising two or more alleles. In some cases, the two or more alleles comprise a minor allele. In particular embodiments, genomic regions of interest comprise one or more HLA loci.

Enrichment of target polynucleotides can be by any means known in the art or otherwise described herein. For example, nucleic acids can be enriched using target-specific primers, or by hybridization to target-selective probes. Target-selective probes can comprise a nucleic acid sequence that is selectively hybridizable to a target polynucleotide of interest. The target-selective probes can comprise a capture moiety which enables capture by a capture reagent. Exemplary capture moiety/reagents include, e.g., biotin/avidin, streptavidin, neutravidin, digoxigenin/wheat germ agglutinin, histidine/cobalt, iron. Nucleic acids can be enriched by a target-selective sequencing library preparation method. Target-selective sequencing library preparation kits and technology are commercially available from, e.g., NuGEN, Agilent, Illumina, or Nimblegen. Target-selective sequencing library preparation methods from Agilent are described in, e.g., U.S. Pat. No. 7,867,703 and US Patent Application Publication No. 20120289426, which are hereby incorporated by reference. Target-selective sequencing library preparation methods from Illumina are described in, e.g., US Patent Application Pub No. 20070141604, hereby incorporated by reference. Target-selective sequencing library preparation methods from Nimblegen are described in, e.g., US Patent Application Pub. No. 20090105081, hereby incorporated by reference. Target-selective sequencing library preparation methods from NuGEN are described in, e.g., US Patent Application Pub. No. 20130231253, hereby incorporated by reference. Other exemplary target-selective sequencing library preparation methods are described in US Patent Application Publication No. 20120003657, hereby incorporated by reference. Enrichment of target genomic regions can, in some cases, comprise isolation of intact chromosomes or chromosomal regions from a biological sample. In some embodiments, the nucleic acid sample is not enriched for target polynucleotides, e.g., represents a whole genome.

The nucleic acid template to be sequenced can be a member of a sequencing library. Sequencing libraries can comprise any number of library members. Sequencing libraries can comprise 2, 10, 50, 100, 500, 1000, 5000, 10,000, 50000, 100000, 500000, 1000000, 5000000, 10000000, 50000000, 100000000, 500000000, 1000000000, 2000000000, 3000000000, 4000000000, 5000000000, 6000000000, 7000000000, 8000000000, 9000000000, 10000000000, or more than 10000000000 members. In some embodiments, nucleic acid libraries are sequenced according to one or more methods described herein. The sequencing library can be prepared from a nucleic acid sample by any means known to those of skill in the art or otherwise described herein. In some embodiments, library preparation comprises attachment of one or more adaptor oligonucleotides to one or more ends of nucleic acid fragments. In some cases, adaptor oligonucleotides are attached to both ends of nucleic acid fragments. The term "adaptor", as used herein, can refer to an oligonucleotide. In some cases, the attachment of an adaptor to a nucleic acid template can enable the generation of amplification-ready products of the nucleic acid template. An adaptor can have various designs. In some embodiments, an adaptor comprises a primer binding site for a platform-specific sequencing primer. In some embodiments, an adaptor comprises a barcode sequence. The barcode sequence can be a unique sequence of nucleotides that can encode information about an assay. A barcode sequence can, for example, encode information relating to the identity of an interrogated allele, identity of a target region of interest, identity of a sample, identity of a subject, or any combination thereof.

Attachment of adaptor oligonucleotides to nucleic acid fragments can be by any means known in the art, including, e.g., hybridization, amplification, ligation, and the like. Various ligation processes and reagents are known in the art and can be useful for attachment of adaptor oligonucleotides to nucleic acid fragments. For example, blunt ligation can be employed. Similarly, a single dA nucleotide can be added to the 3'-end of the double-stranded DNA product, by a polymerase lacking 3'-exonuclease activity and can anneal to an adaptor comprising a dT overhang (or the reverse). This design allows the hybridized components to be subsequently ligated (e.g., by T4 DNA ligase). Other ligation strategies and the corresponding reagents and known in the art and kits and reagents for carrying out efficient ligation reactions are commercially available (e.g, from New England Biolabs, Roche).

In some cases, it is useful to preserve information about the direction of single-stranded nucleic acid molecules while generating double-stranded polynucleotides. This may be accomplished by creation of a strand specific, e.g., directional sequencing library. The term "strand specific" or "directional", as used herein, can refer to the ability to differentiate in a double-stranded polynucleotide between the original template strand and the strand that is complementary to the original template strand. In some cases, one of the strands of the double-stranded polynucleotide is synthesized so that it has at least one modified nucleotide incorporated into it along the entire length of the strand. In some embodiments, the incorporation of the modified nucleotide marks the strand for degradation or removal. In some embodiments, the methods provided herein contemplate construction of directional nucleic acid libraries as described in pending U.S. application Ser. No. 13/643,056, titled COMPOSITIONS AND METHODS FOR DIRECTIONAL NUCLEIC ACID AMPLIFICATION AND SEQUENCING, Ser. No. 13/643,056, hereby incorporated by reference in its entirety. In some cases, information about the direction of single-stranded nucleic acid molecules is not preserved while generating double-stranded polynucleotides. In some cases, the sequencing library is not a directional sequencing library.

Nucleic acid library members can optionally be amplified prior to sequencing. Methods of amplification are well known in the art. In some embodiments, the amplification is exponential, e.g. in the enzymatic amplification of specific double stranded sequences of DNA by a polymerase chain reaction (PCR). In other embodiments the amplification method is linear.

In other embodiments the amplification method is isothermal. In some embodiments, the amplification comprises digital PCR. The digital PCR can be droplet digital PCR. In some embodiments, the amplification comprises single primer isothermal amplification (SPIA). In some embodiments, the amplification comprises reverse transcription PCR. In some embodiments, the amplification comprises real-time PCR. In some embodiments, the amplification comprises quantitative PCR (Q-PCR).

Nucleic acid library members can be clonally amplified prior to sequencing. Clonal amplification can involve generation of identical copies of individual nucleic acid templates in a nucleic acid library. Nucleic acid templates can be clonally amplified by any means known to those of skill in the art or otherwise described herein. In some cases, clonal amplification can comprise spatial separating individual nucleic acid template molecules and performing amplification of the separated nucleic acid template molecules. In certain instances, clonal amplification can comprise emulsion PCR (454 Life Sciences, Life Technologies). Emulsion PCR can comprise attachment of an individual nucleic acid template to a bead or particle. Beads and/or particles can be isolated in a water-in-oil emulsion, wherein droplets of the water-in-oil emulsion comprise a bead or particle with a template molecule attached thereon, and reaction components for carrying out an amplification reaction Amplification of templates within the emulsion can result in clonal amplification of the templates. Clonal amplification can comprise bridge amplification (Illumina, Inc.). Bridge amplification is described, e.g, in U.S. Pat. No. 7,985,565, which is hereby incorporated by reference. Clonal amplification can comprise template walking (Life Technologies), described in US Patent Application Publication No. 20120156728, hereby incorporated by reference.

Primers

Primers can be oligonucleotides that are employed in an extension reaction by a polymerase along a polynucleotide template, such as in PCR or cDNA synthesis, for example. An oligonucleotide primer can be a synthetic polynucleotide that is single stranded, containing a sequence at its 3'-end that is capable of hybridizing with a sequence of the target polynucleotide. In some cases, the 3' region of the primer that hybridizes with the target nucleic acid has at least 80%, 90%, 95%, or 100% complementarity to a sequence or primer binding site.

Primers can be sufficiently long to prime synthesis of an extension strand along a template. Primers used in one or more methods described herein can have a length. The length can be any length, e.g., about 5 to about 15 nt, about 10 to about 20 nt, about 15 to about 30 nt, about 20 to about 40 nt, about 30 to about 60 nt, about 50 to about 100 nt, or more than about 100 nt.

Primers used in one or more methods described herein can include primers designed to hybridize to a portion or all of a sequencing adaptor. In some cases, primers described herein are designed to hybridize to a primer-binding sequence of a sequencing adaptor. Exemplary adaptors are described herein. In some cases, a first sequencing primer to be used in a sequential sequencing method (e.g., primer or primers to be used in a first round of sequencing) is designed to hybridize to a portion or all of a sequencing adaptor.

Primers used in one or more methods can include primers designed to sequence one or more loci from which phasing information is desired. The one or more loci can comprise one or more informative loci. For example, in some cases, the first sequencing primer, second sequencing primer (e.g., primer or primers to be used in a first or second round of sequencing, respectively), or any subsequent sequencing primer used in a sequential sequencing method is designed to sequence an informative locus.

A primer designed to sequence an informative locus can be designed to hybridize to a genomic location that is a distance upstream of the informative locus to be sequenced. The distance can be of any length. A skilled artisan will readily appreciate that the distance can vary depending on the read length of the sequencing technology utilized in the sequential sequencing method. In some cases, the distance is shorter than a read length of the sequencing technology utilized in the sequential sequencing method. The primer designed to sequence an informative locus can be designed to hybridize to a genomic location that is about, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10000, 100000, or more than 100000 nt upstream of the informative locus. The primer designed to sequence an informative locus can be designed to hybridize to a genomic location that is about 1 to about 10, about 5 to about 50, about 20 to about 100, about 40 to about 200, about 80 to about 500, about 100 to about 1000, about 500 to about 10000, about 5000 to about 100000, or more than 100000 nt upstream of the informative locus.

In some cases, the primer designed to sequence an informative locus can be designed to hybridize to a conserved region of the genome. The conserved region can be a region that does not comprise a polymorphic locus, e.g., is substantially not polymorphic. In some embodiments, the conserved region exhibits a polymorphism (e.g., sequence variant) at a population frequency that is less than 5%, less than 4%, less than 3%, less than 2%, less than 1%, less than 0.9%, less than 0.8%, less than 0.7%, less than 0.6%, less that 0.5%, less than 0.4%, less than 0.3%, less than 0.2%, less than 0.1%, less than 0.05%, less than 0.01%, less than 0.05%, less than 0.001%, less than 0.005%, less than 0.0001%, %, less than 0.0005%, less than 0.00001%,%, less than 0.00005%, less than 0.000001%, less than 0.000005%, less than 0.0000001%, less than 0.0000005%, or less than 0.00000001%. In some cases, the primer designed to sequence an informative locus can be designed to hybridize to an unconserved region of the genome.

Primers used in a first, second, or additional round of sequencing can hybridize to distinct locations on the nucleic acid template. For example, a first primer used in a first round of sequencing may comprise a 3' terminal nucleotide that hybridizes to a first location of a nucleic acid template. A second primer used in a second round of sequencing may comprise a 3' terminal nucleotide that hybridizes to a second location that is more than 5 nt away from the first location of the nucleic acid template (e.g., hybridizes to a location that is at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10000, 100000, or more than 100000 nt away from the first location of the nucleic acid template. In some cases, a third primer used in a third round of sequencing may comprise a 3' terminal nucleotide that hybridizes to a third location that is more than 5 nt away from the second location of the nucleic acid template (e.g., hybridizes to a nucleotide that is at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10000, 100000, or more than 100000 nt away from the second location of the nucleic acid template. Any primer used in a subsequent round of sequencing can have a 3' terminal nt that hybridizes to a location of the nucleic acid template that is at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10000, 100000, or more than 100000 nt away from a binding site of the 3' terminal nt of the previous sequencing primer used in the previous round of sequencing.

Primers used in a first, second, or additional round of sequencing can initiate sequencing at distinct locations on the nucleic acid template. For example, a first primer used in a first round of sequencing may initiate sequencing at a first location of a nucleic acid template. A second primer used in a second round of sequencing may initiate sequencing at a second location that is more than 5 nt away from the first location of the nucleic acid template (e.g., initiates sequencing at a location that is at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10000, 100000, or more than 100000 nt away from the first location of the nucleic acid template. In some cases, a third primer used in a third round of sequencing may initiate sequencing at a third location that is more than 5 nt away from the second location of the nucleic acid template (e.g., initiates sequencing at a location that is at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10000, 100000, or more than 100000 nt away from the second location of the nucleic acid template. Any primer used in a subsequent round of sequencing can initiate sequencing at a location of the nucleic acid template that is more than 5 nt away from the location of initiated sequencing for the previous round of sequencing, e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10000, 100000, or more than 100000 nt away from the location of initiated sequencing for the previous round of sequencing.

In some embodiments, standard or universal sequencing primers are used. For example, primers designed to hybridize to a primer binding site of a sequencing adaptor can be used. A primer can be a polyA or polyT oligonucleotide. In some embodiments, sequence-specific primers that hybridize to a conserved region or conserved regions within the nucleic acid inserts in the sequencing library are used. In some embodiments, the sequence-specific primers are designed to hybridize to conserved regions adjacent to regions of variable sequence within the nucleic acid inserts, thereby enabling differentiating between closely related sequences. In some embodiments, a set of oligonucleotide primers that hybridize to sequences shared in closely related sequences, such as gene/pseudogene pairs, are used.

Primers can be prepared by any suitable method. Methods for preparing oligonucleotides of specific sequence are known in the art, and include, for example, cloning and restriction of appropriate sequences or direct chemical synthesis. Chemical synthesis methods may include, for example, the phosphodiester method disclosed by Brown et al., 1979, Methods in Enzymology 68:109, the phosphotriester method described by Narang et al., 1979, Methods in Enzymology 68:90, the diethylphosphoramidate method disclosed in Beaucage et al., 1981, Tetrahedron Letters 22:1859, and the solid support method disclosed in U.S. Pat. No. 4,458,066, all of which publications are hereby incorporated by reference. Primers and/or reporter probes can also be obtained from commercial sources such as Amersham Pharmacia Biotech, Operon Technologies, Sigma, IDT Technologies, and Life Technologies. Computer programs can also be used to design primers, including but not limited to Array Designer Software (Arrayit Inc.), NetPrimer, Oligonucleotide Probe Sequence Design Software for Genetic Analysis (Olympus Optical Co.), Primer3, and DNAsis from Hitachi Software Engineering.

Methods of Sequencing

The methods provided herein contemplate sequential sequencing of nucleic acid templates. Sequencing methods are also well known in the art. Sequencing can be performed by a sequencing platform. The sequencing platform can be a next-generation sequencing (NGS) platform. In some cases, the NGS platform can sequence clonally amplified DNA templates or single DNA molecules in a massively parallel fashion (e.g. as described in Volkerding et al. Clin Chem 55:641-658 [2009]; Metzker M Nature Rev 11:31-46 [2010]), hereby incorporated by reference. Sequential sequencing methods provided herein can also employ Sanger sequencing.

The next-generation sequencing platform can be a commercially available platform. Commercially available platforms useful for performing a method described herein include, e.g., platforms for sequencing-by-synthesis, ion semiconductor sequencing (ChemFET sequencing), reversible dye terminator sequencing, pyrosequencing, sequencing by ligation, single-molecule sequencing, and sequencing by hybridization.

Platforms for sequencing by synthesis are available from, e.g., 454 Life Sciences, Illumina, Helicos Biosciences, and Qiagen. Illumina platforms can include, e.g., Illumina's Solexa platform, Illumina's Genome Analyzer, Illumina's MiSeq, Illumina's HiSeq, Illumina's NextSeq, and are described in Gudmundsson et al (Nat. Genet. 2009 41:1122-6), Out et al (Hum. Mutat. 2009 30:1703-12) and Turner (Nat. Methods 2009 6:315-6), U.S. Patent Application Publication Nos. 20080160580 and 20080286795, U.S. Pat. Nos. 6,306,597, 7,115,400, and 7,232,656, which are hereby incorporated by reference. 454 Life Science platforms include, e.g., the GS Flex and GS Junior, and are described in U.S. Pat. No. 7,323,305, hereby incorporated by reference. Platforms for ion semiconductor sequencing include, e.g., the Ion Torrent Personal Genome Machine (PGM) and are described in U.S. Pat. No. 7,948,015, hereby incorporated by reference. Platforms for pryosequencing include the GS Flex 454 system and are described in U.S. Pat. Nos. 7,211,390; 7,244,559; 7,264,929, hereby incorporated by reference. Platforms for sequencing by ligation include, e.g., the SOLiD sequencing platform and are described in U.S.
Pat. No. 5,750,341, hereby incorporated by reference. Platforms for single-molecule sequencing include the SMRT system from Pacific Bioscience and the Helicos True Single Molecule Sequencing platform.

For example, a sequencing technique that can be used in one or more phasing methods described herein is the method commercialized by Illumina, as described, e.g., in U.S. Pat. Nos. 5,750,341; 6,306,597; and 5,969,119. Such method can employ cluster amplification of library members onto a flow cell and a sequencing-by-synthesis approach. In a round of sequencing, cluster-amplified library members can be subjected to repeated cycles of polymerase-directed single base extension. Single-base extension can involve incorporation of reversible-terminator dNTPs, each dNTP labeled with a different removable fluorophore. The reversible-terminator dNTPs can be 3' modified to prevent further extension by the polymerase. After incorporation of the dNTP, the incorporated nucleotide can be identified by fluorescence imaging. Following fluorescence imaging, the fluorophore can be removed and the 3' modification can be removed resulting in a 3' hydroxyl group, thereby allowing another cycle of single base extension.

In one embodiment of a phasing method employing Illumina sequencing methodology, a sequencing library is prepared from a nucleic acid sample obtained from a subject. In some cases, the sequencing library is a directional sequencing library. In some cases, the sequencing library is not a directional sequencing library. Single-stranded nucleic acids from the library can optionally be amplified, for example, by PCR, prior to coupling to the Illumina sequencing platform. To couple template nucleic acids to the Illumina platform, the nucleic acids can be denatured into single-stranded templates. The single-stranded templates can be randomly attached to the inside surface of flow-cell channels. In some embodiments the single-stranded templates are randomly attached to unique addressable locations of the flow-cell. Unlabeled nucleotides can be added to initiate solid-phase bridge amplification to produce dense clusters of clonally amplified templates. In some embodiments, each cluster is coupled to a unique addressable location of the flow-cell. To initiate a first round of sequencing, labeled reversible terminator dNTPs, a first sequencing primer, and DNA polymerase can be added to the Illumina flow cell. The clusters can be subjected to repeated cycles of polymerase-directed single base extension and label detection as described above, thereby producing a first sequencing read from one or more clusters. Upon completion of the first round of sequencing, the extended strands and sequencing primers can be denatured from the cluster templates and removed, e.g., by washing. To initiate a second round of sequencing, labeled reversible terminator dNTPS, a second sequencing primer, and DNA polymerase can be added to the Illumina flow cell. The clusters can then be subjected to repeated cycles of polymerase-directed single base extension and label detection as described above, thereby producing a second sequencing read from one or more clusters. Subsequent rounds of sequencing can optionally be performed by removing the extended strands and primers from the preceding round of sequencing, using subsequent primers that are designed to hybridize, for example, downstream or upstream of the preceding sequencing primer. Sequence reads for the first, second, and optionally additional rounds of sequencing can be compiled for each cluster. The compiling can be used to generate sequence information for the clonally amplified templates. Sequence information for the clonally amplified templates can be used to determine phasing of one or more alleles detected by the sequencing.

In some embodiments, one or more phasing methods described herein employ sequencing by ligation methods commercialized by Applied Biosystems (e.g., SOLiD sequencing). Library preparation for SOLiD sequencing can comprise ligation of adaptors attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, nucleic acid templates can be clonally amplified on beads via PCR. Following PCR, the templates can be denatured. Beads can be enriched for beads with extended templates. The clonally amplified templates on the beads can be subjected to a 3' modification that permits bonding to a glass slide. The beads can be deposited on a glass slide for sequencing by ligation. In some embodiments, each bead is deposited onto a unique addressable location of the glass slide. A round of SOLiD sequencing can comprise the following steps: (1) hybridization of a first sequencing primer to the clonally amplified templates. The first sequencing primer can be designed to hybridize to a sequencing primer binding site on one or more adaptors attached to the template nucleic acids. (2) Following hybridization, a set of four fluorescently labeled di-base probes can compete for ligation to the sequencing primer. Specificity of the di-base probe can be achieved by interrogating every 1st and 2nd base in each ligation reaction. (3) Cycles of ligation, detection and cleavage can be performed with the number of cycles determining the eventual read length. (4) Following a series of ligation cycles, the extension product can be removed and the template can be reset with a primer complementary to the n−1 position for a second round of ligation cycles. For SOLiD sequencing, one round of sequencing can comprise five rounds of primer reset and ligation cycles as described above, wherein each subsequent primer hybridizes to an n−1 position of the adaptor sequencing.

In one embodiment of a phasing method described herein employing SOLiD sequencing methodology, a sequencing library is prepared from a nucleic acid sample obtained from a subject using a library preparation method for SOLiD sequencing as described herein. In some cases, the sequencing library is a directional sequencing library. In some cases, the sequencing library is not a directional sequencing library. The sequencing library members can be deposited onto unique addressable locations of the SOLiD platform as described herein. A first round of SOLiD sequencing can be performed as described herein. Following the first round of sequencing, the extension product can be removed and a second set of sequencing primers can be used for a second round of SOLiD sequencing. The second round of SOLiD sequencing can comprise multiple cycles of primer hybridization and ligation as described above. The second set of sequencing primers can comprise a primer "primer A" that is designed to hybridize to a genomic location residing 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more than 50 nucleotides upstream of an informative locus "A" as well as 2, 3, 4, 5, or more additional sequencing primers that are designed to hybridize to an n−1 genomic location, n−2 genomic location, n−3 genomic location, n−4 genomic location, n−5 genomic location, etc., of "Primer A" Following a second round of SOLiD sequencing, the extension product can be removed and a third set of sequencing primers can be used for a third round of SOLiD sequencing. The third set of sequencing primers can comprise a primer "primer B" that is designed to hybridize to a genomic location residing 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more than 50 nucleotides upstream of an informative locus "B", as well as 2, 3, 4, 5, or more additional sequencing primers that are designed to hybridize to an n−1 location, n−2 location, n−3 location, n−4 location, n−5 location, etc., of "Primer B". The informative locus "B" can be located downstream or upstream of informative locus "A". The third round of SOLiD sequencing can comprise multiple cycles of primer hybridization and ligation as described above. Additional rounds of SOLiD sequencing can be performed to sequence further downstream informative loci, as described above. Sequence reads for the first, second, and optionally additional rounds of sequencing can be compiled for each addressable location. The compiling can be used to generate sequence information for the clonally amplified templates. Sequence information for the clonally amplified templates can be used to determine phasing of one or more alleles detected by the sequencing.

In other embodiments, one or more phasing methods disclosed herein employ sequencing by synthesis using the methods commercialized by 454/Roche Life Sciences, including but not limited to the methods and apparatus described, e.g., in Margulies et al., Nature (2005) 437:376-380 (2005); and U.S. Pat. Nos. 7,244,559; 7,335,762; 7,211,390; 7,244,567; 7,264,929; and 7,323,305, hereby incorporated by reference. 454 sequencing library preparation can comprise ligation of adaptors to the ends of nucleic acid fragments. The adaptors can serve as primers for amplification and can provide a sequencing primer binding site for sequencing-by-synthesis. One of the adaptors can comprise a capture reagent, e.g., a biotin. The nucleic acid fragments can be attached to capture beads, e.g., streptavidin-coated beads. The fragments attached to the beads can be PCR amplified within droplets of an oil-water emulsion, resulting in multiple copies of clonally amplified nucleic acid fragments on each bead. Following 454 library preparation, library members can be coupled to a 454 sequencing platform by capture of beads in wells of the 454 platform, which can be pico-liter sized. In some cases, a well captures one bead. Each well can accordingly be an addressable location of the 454 platform. Pyrosequencing can be performed on each DNA fragment in parallel. Pyrosequencing can comprise hybridization of a sequencing primer to a sequencing primer binding site on an adaptor, followed by extension of the primer in a pyrosequencing reaction. During the pyrosequencing reaction, dTNPs are added such that only one out of four of the possible A/T/C/G nucleotides are added and available at a time. Pyrosequencing can detect release of pyrophosphate (PPi) upon nucleotide incorporation. PPi can be converted to ATP by ATP sulfurylase in the presence of adenosine 5' phosphosulfate. Luciferase can use ATP to convert luciferin to oxyluciferin, thereby generating a light signal that is detected. A detected light signal can be used to identify the incorporated nucleotide. The intensity of the light signal can be used to determine how many bases are incorporated. Following detection of the light signal, unincorporated dNTPs can be removed and the next one out of four possible A/T/C/G nucleotides can be added.

In one embodiment of a phasing method employing pyrosequencing methodology (e.g., 454 sequencing), a sequencing library is prepared from a nucleic acid sample obtained from a subject. In some cases, the sequencing library is a directional sequencing library. In some cases, the sequencing library is not a directional sequencing library. Sequencing library members can be coupled to addressable locations of a pyrosequencing platform (e.g., a 454 sequencing platform) as described above. A first round of pyrosequencing can be performed as described above, generating a first sequencing read from the library members. Following the first round of pyrosequencing, the extension strands and primers are removed from the library members, e.g., by denaturation and washing. A second round of sequencing can then be performed by hybridization of a second sequencing primer to one or more library members. The second sequencing primer can be designed to hybridize to a location upstream of an informative locus "A" and to sequence informative locus "A". A second pyrosequencing reaction can then be performed as described above. Subsequent removal of the second sequencing primer and additional rounds of pyrosequencing can be performed to sequence additional informative loci. The additional informative loci can be located downstream or upstream of locus "A". Sequence reads for the first, second, and optionally additional rounds of sequencing can be compiled for each addressable location. The compiling can be used to generate sequence information for the clonally amplified templates. Sequence information for the clonally amplified templates can be used to determine phasing of two or more alleles detected by the sequencing.

In other embodiments, one or more phasing methods disclosed herein may employ the sequencing methods commercialized by Helicos BioSciences Corporation (Cambridge, Mass.) as described, e.g., in U.S. patent application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058, hereby incorporated by reference. For example, a method can employ the true Single-Molecule Sequencing technology by Helicos Biosciences Corporation. tSMS library preparation can comprise ligation of a polyA adaptor to 3' end of DNA fragments. The adapted fragments can then be coupled to a Helicos tSMS sequencer by the following steps: (1) fragments are hybridized to poly-T oligonucleotides immobilized on the tSMS flow cell; (2) the flow cell is loaded into an instrument, e.g., HeliScope™ sequencer. Each fragment can be hybridized to a unique addressable location on the tSMS flow cell. A laser can illuminate the surface of the flow cell, revealing the position of each template. A CCD camera can map the position of the templates on the flow cell surface. tSMS sequencing can then proceed by subjecting library members to repeated cycles of polymerase-directed single base extension. A round of tSMS sequencing reaction can commence by introducing a DNA polymerase and a fluorescently labeled nucleotide. The polymerase can incorporate the labeled nucleotides to the primer in a template directed manner. The polymerase and unincorporated nucleotides can be removed. The templates that have directed incorporation of the fluorescently labeled nucleotide can be discerned by imaging the flow cell surface. After imaging, a cleavage step can remove the fluorescent label, and the process can be repeated with other fluorescently labeled nucleotides until a desired read length is achieved. Sequence information can be collected with each nucleotide addition step.

In one embodiment of a phasing method employing the Helicos tSMS methodology, a tSMS sequencing library is prepared as described above from a nucleic acid sample obtained from a subject. In some cases, the sequencing library is a directional sequencing library. In some cases, the sequencing library is not a directional sequencing library. The sequencing library members can be coupled to unique addressable locations on the tSMS platform as described herein, e.g., by hyridization to polyT oligonucleotides immobilized on the flow cell. Reverse complement complement strands of the hybridized library members can be synthesized, thus creating immobilized templates for sequencing. The original library members hybridized to the flowcell can be denatured and/or removed. A first round of tSMS sequencing can be performed on immobilized templates as described above, generating a first sequencing read from the immobilized templates. Following the first round of tSMS sequencing, the first sequencing reads can be denatured and/or removed. The immobilized templates can be retained on the flow cell. A second round of tSMS sequencing can then be performed by hybridization of a sequencing primer to the immobilized templates. The second sequencing primer can be designed to hybridize to a location upstream of an informative locus "A" and to sequence informative locus "A". A second tSMS sequencing reaction can then be performed as described above. Subsequent denaturation and/or removal of the sequencing primer and sequence reads, followed by additional rounds of tSMS sequencing can be performed on the immobilized templates to sequence additional informative loci. The additional informative loci can be located downstream or upstream of locus "A". Sequence reads for the first, second, and optionally additional rounds of sequencing can be compiled for each addressable location. The compiling can be used to generate sequence information for the templates. Sequence information for the templates can be used to determine phasing of one or more alleles detected by the sequencing.

Another example of a sequencing technique that can be used in the methods described herein is semiconductor sequencing provided by Ion Torrent (e.g., using the Ion Personal Genome Machine (PGM)). Ion Torrent technology can use a semiconductor chip with multiple layers, e.g., a layer with micro-machined wells, an ion-sensitive layer, and an ion sensor layer. Sequencing library preparation for the Ion Torrent platform can involves ligation of two distinct adaptors at both ends of a DNA fragment. Individual library members can be attached to beads, as described herein. The library members can then be clonally amplified by, e.g., emulsion PCR. The clonally amplified library members can be coupled to an Ion Torrent sequencing platform, for example, by introducing individual beads comprising the clonally amplified library members into wells of the Ion Torrent platform. Each well can be considered a unique addressable location of the Ion Torrent platform. A round of sequencing can comprise annealing a first sequencing primer to the library members. The first sequencing primer can be designed to hybridize to a sequencing primer binding region of an Ion Torrent library adaptor. To initiate sequencing of the nucleic acids on the beads, one type of deoxyribonucleotide (e.g., dATP, dCTP, dGTP, or dTTP) can be introduced into the wells. When one or more nucleotides are incorporated by DNA polymerase, protons (hydrogen ions) can be released in the well, which can be detected by the ion sensor. The semiconductor chip can then be washed and the process can be repeated with a different deoxyribonucleotide. A plurality of nucleic acids can be sequenced in the wells of a semiconductor chip. The semiconductor chip can comprise chemical-sensitive field effect transistor (chemFET) arrays to sequence DNA (for example, as described in U.S. Patent Application Publication No. 20090026082). Incorporation of one or more triphosphates into a new nucleic acid strand at the 3' end of the sequencing primer can be detected by a change in current by a chemFET. An array can have multiple chemFET sensors.

In one embodiment of a phasing method described herein employing Ion Torrent methodology, an Ion Torrent sequencing library is prepared as described above from a nucleic acid sample obtained from a subject. In some cases, the sequencing library is a directional sequencing library. In some cases, the sequencing library is not a directional sequencing library.

Sequencing library members can be coupled to unique addressable locations of the Ion Torrent platform as described herein. A first round of Ion Torrent sequencing can be performed on library members as described above, generating a first sequencing read from the library members. Upon completion of the first round of sequencing, the extended strands and sequencing primers can be denatured from the templates and removed, e.g., by washing. A second round of sequencing can be performed using a second sequencing primer. The second sequencing primer can be designed to hybridize to a location upstream of an informative locus "A" and to sequence informative locus "A". A second sequencing reaction can then be performed as described above. Subsequent removal of the second sequencing primer and additional rounds of sequencing can be performed to sequence additional informative loci. The additional informative loci can be located downstream or upstream of locus "A". Sequence reads for the first, second, and optionally additional rounds of sequencing can be compiled for each addressable location. The compiling can be used to generate sequence information for the clonally amplified templates. Sequence information for the clonally amplified templates can be used to determine phasing of one or more alleles detected by the sequencing.

Sequential sequencing by any of the means described herein can produce one or more sequencing reads for nucleic acid templates. The sequencing reads can have a length which may vary depending on the particular sequencing technology utilized. NGS platforms can provide sequence reads that vary in size from 1, 2, 3, 4, 5, 6, 7, 8, 9, 10, tens to hundreds, or thousands of base pairs. In some embodiments of the method described herein, the sequence reads are about 1 base long, about 2 bases long, about 3 bases long, about 4 bases long, about 5 bases long, about 6 bases long, about 7 bases long, about 8 bases long, about 9 bases long, about 10 bases long, about 12 bases long, about 14 bases long, about 16 bases long, about 18 bases long, about 20 bases long, about 25 bases long, about 30 bases long, about 35 bases long, about 40 bases long, about 45 bases long, about 50 bases long, about 55 bases long, about 60 bases long, about 65 bases long, about 70 bases long, about 75 bases long, about 80 bases long, about 85 bases long, about 90 bases long, about 95 bases long, about 100 bases long, about 110 bases long, about 120 bases long, about 130, about 140 bases long, about 150 bases long, about 200 bases long, about 250 bases long, about 300 bases long, about 350 bases long, about 400 bases long, about 450 bases long, about 500 bases long, about 600 bases long, about 700 bases long, about 800 bases long, about 900 bases long, about 1000 bases, about 2000 bases, about 3000 bases, about 4000 bases, about 5000 bases, about 6000 bases, about 7000 bases, about 8000 bases, about 9000 bases, about 10,000 bases long, about 20,000 bases long, about 30,000 bases long, about 40,000 bases long, about 50,000 bases long, about 60,000 bases long, about 70,000 bases long, about 80,000 bases long, about 90,000 bases long, about 100,000 bases, about 150,000 bases long, about 200,000 bases long, about 250,000 bases long, or more than 250,000 bases long.

In some cases, a sequencing read is at least 1 base long, at least 2 bases long, at least 3 bases long, at least 4 bases long, at least 5 bases long, at least 6 bases long, at least 7 bases long, at least 8 bases long, at least 9 bases long, at least 10 bases long, at least 12 bases long, at least 14 bases long, at least 16 bases long, at least 18 bases long, at least 20 bases long, at least 25 bases long, at least 30 bases long, at least 35 bases long, at least 40 bases long, at least 45 bases long, at least 50 bases long, at least 55 bases long, at least 60 bases long, at least 65 bases long, at least 70 bases long, at least 75 bases long, at least 80 bases long, at least 85 bases long, at least 90 bases long, at least 95 bases long, at least 100 bases long, at least 110 bases long, at least 120 bases long, at least 130 bases long, at least 140 bases long, at least 150 bases long, at least 200 bases long, at least 250 bases long, at least 300 bases long, at least 350 bases long, at least 400 bases long, at least 450 bases long, at least 500 bases long, at least 600 bases long, at least 700 bases long, at least 800 bases long, at least 900 bases long, at least 1000 bases long, at least 10,000 bases long, at least 20,000 bases long, at least 30,000 bases long, at least 40,000 bases long, at least 50,000 bases long, at least 60,000 bases long, at least 70,000 bases long, at least 80,000 bases long, at least 90,000 bases long, at least 100,000 bases, at least 150,000 bases long, at least 200,000 bases long, or more than 200,000 bases long.

A sequencing read can be between about 1 to about 10 bases long, between about 5 to about 50 bases long, between about 20 to about 100 bases long, between about 50 to about 200 bases long, between about 100 to about 500 bases long, between about 200 to about 1000 bases long, between about 500 to about 2000 bases long, between about 1000 to about 5000 bases long, between about 2000 to about 10000 bases long, between about 5000 to about 50000 bases long, a between about 10000 to about 100000 bases long, or more than 100000 bases long.

Sequence Analysis

Sequencing reads (e.g., sequence tags) can be aligned to assemble a partial or complete map of the subject's genome. Sequence tags can be aligned (e.g., mapped), for example, to a reference genome. The reference genome can be a human reference genome. The human reference genome can be the NCBI36/hg18 sequence, available on the world wide web at genome.ucsc.edu/cgi-bin/hgGateway?org=Human&db=hg18&hgsid=166260105).

Sequencing reads can be mapped using an alternative source of public sequence information. Other sources of public sequence information include GenBank, dbEST, dbSTS, EMBL (the European Molecular Biology Laboratory), and the DDBJ (the DNA Databank of Japan). In some cases, the reference genome can be an artificial target sequence genome comprising polymorphic target sequences.

Mapping of the sequence tags can be achieved, for example, by aligning the sequence of the tag to a sequence of the reference genome. Such methods can be used to map a sequencing read to a genomic region, a chromosomal region, or a chromosome. A number of computer algorithms can be used for aligning sequences. Such algorithms include, without limitation, BLAST (Altschul et al., 1990), BLITZ (MPsrch) (Sturrock & Collins, 1993), BOWTIE (Langmead et al, Genome Biology 10:R25.1-R25.10 [2009]), FASTA (Person & Lipman, 1988), SAMtools (SAMtools, Bioinformatics, 2009, 25(16):2078-9), and ELAND (Illumina, Inc., San Diego, Calif., USA). In one embodiment, sequence reads produced by Illumina sequencing are processed by bioinformatic alignment analysis for the Illumina Genome Analyzer, which uses the Efficient Large-Scale Alignment of Nucleotide Databases (ELAND) software. Additional software includes the Burroughs-Wheeler block sorting compression procedure which involves block sorting or preprocessing to make compression more efficient.

Reads from the sequential rounds of sequencing can be compiled for each sequenced template to assemble complete or partial sequence information of the template. Reads from the sequential rounds of sequencing can be compiled according to unique addressable locations of the sequencing platform. For example, all reads generated from a unique addressable location of a sequencing platform can be compiled into a data file. Reads can be compiled with aid of a computer processor. Compiled reads from a unique addressable location can be used to determine partial or complete sequence information for a nucleic acid template (either single template or clonally amplified template). The partial or complete sequence information can comprise information over a longer distance than an average read length of the sequencing platform. Because the sequence information is over a longer distance than an average read length of the sequencing platform, the probability that the sequence information comprises information over two or more informative loci can be increased.

Compiled reads from a unique addressable location may comprise sequence information for two or more detected alleles. Such compiled reads can be used to determine that the two or more detected alleles are in phase, since the detected alleles are located on the sample template or clonally amplified template. Alleles detected across two or more addressable locations can also be determined to be in phase, if the two or more addressable locations each share at least one detected allele in common Alleles detected across a set of addressable locations comprising any number of addressable locations can be determined to be in phase, if the addressable locations in the set share at least one detected allele in common with at least one other addressable location in the set.

Compiling of reads, determination of phasing information, and/or haplotype analysis can be performed with the aid of a computer system. In some embodiments, the computer system executes instructions contained in a computer-readable medium. The computer system can comprise a processor. The processor can be associated with one or more controllers, calculation units, and/or other units of a computer system, or implanted in firmware. In some embodiments, one or more steps of the method are implemented in hardware. In some embodiments, one or more steps of the method are implemented in software. Software routines may be stored in any computer readable memory unit such as flash memory, RAM, ROM, magnetic disk, laser disk, or other storage medium as described herein or known in the art. Software may be communicated to a computing device by any known communication method including, for example, over a communication channel such as a telephone line, the internet, a wireless connection, or by a transportable medium, such as a computer readable disk, flash drive, etc. The one or more steps of the methods described herein may be implemented as various operations, tools, blocks, modules and techniques which, in turn, may be implemented in firmware, hardware, software, or any combination of firmware, hardware, and software. When implemented in hardware, some or all of the blocks, operations, techniques, etc. may be implemented in, for example, an application specific integrated circuit (ASIC), custom integrated circuit (IC), field programmable logic array (FPGA), or programmable logic array (PLA).

Figure 6:
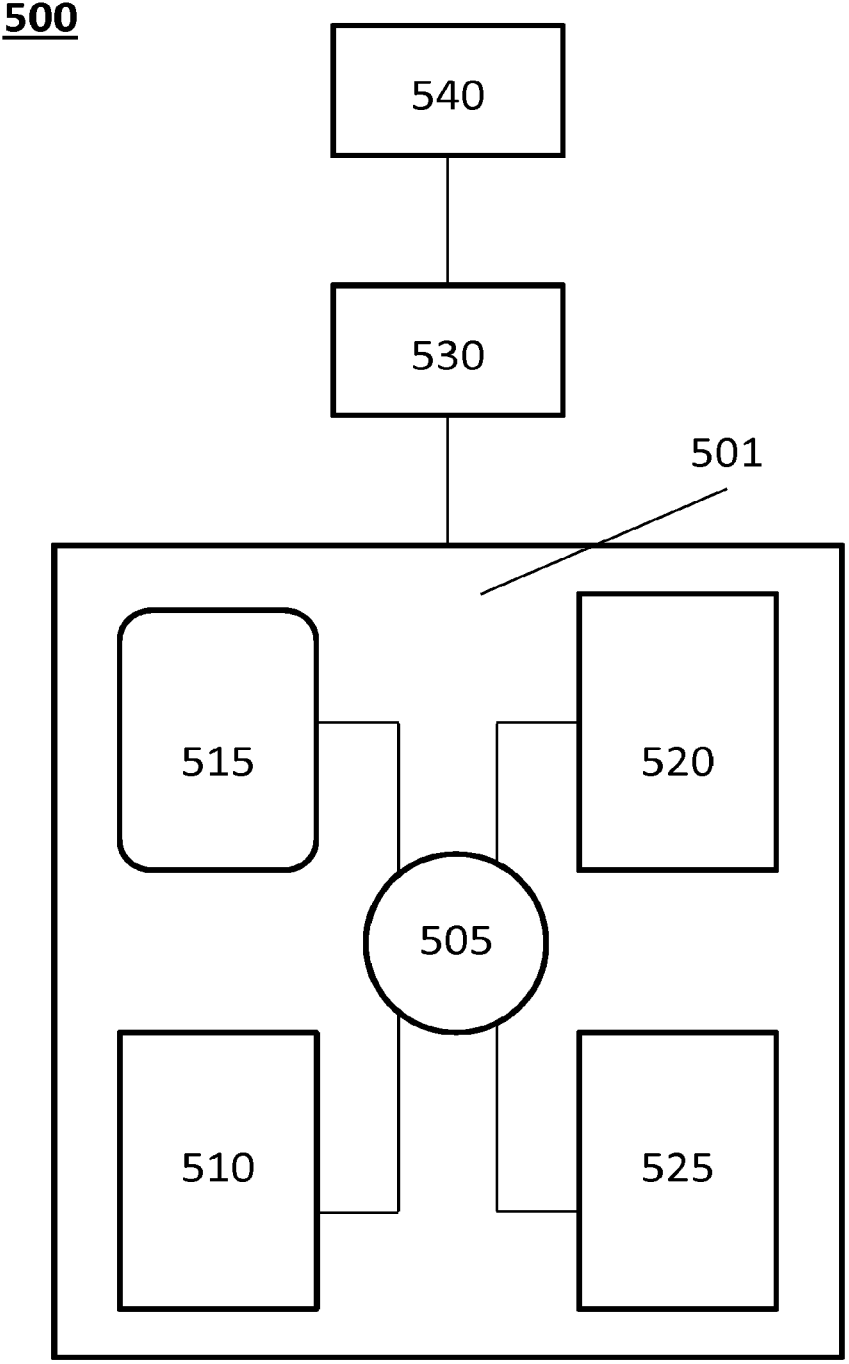
FIG. 6 depicts an exemplary computer system disclosed herein.

FIG. 6 depicts an exemplary computer system adapted to implement one or more methods provided herein. The system 500 includes a central computer server 501 that is programmed to implement exemplary methods described herein. The server 501 includes a central processing unit (CPU, also "processor") 505 which can be a single core processor, a multi core processor, or plurality of processors for parallel processing. The server 501 also includes memory 510 (e.g. random access memory, read-only memory, flash memory); electronic storage unit 515 (e.g. hard disk); communications interface 520 (e.g. network adaptor) for communicating with one or more other systems; and peripheral devices 525 which may include cache, other memory, data storage, and/or electronic display adaptors. The memory 510, storage unit 515, interface 520, and peripheral devices 525 are in communication with the processor 505 through a communications bus (solid lines), such as a motherboard. The storage unit 515 can be a data storage unit for storing data. The server 501 is operatively coupled to a computer network ("network") 530 with the aid of the communications interface 520. The network 530 can be the Internet, an intranet and/or an extranet, an intranet and/or extranet that is in communication with the Internet, a telecommunication or data network. The network 530 in some cases, with the aid of the server 501, can implement a peer-to-peer network, which may enable devices coupled to the server 501 to behave as a client or a server.

The storage unit 515 can store files, such as subject reports, and/or communications with the caregiver, sequencing data, data about individuals, or any aspect of data generated by one or more phasing methods disclosed herein.

The server can communicate with one or more remote computer systems through the network 530. The one or more remote computer systems may be, for example, personal computers, laptops, tablets, telephones, Smart phones, or personal digital assistants.

In some situations the system 500 includes a single server 501. In other situations, the system includes multiple servers in communication with one another through an intranet, extranet and/or the Internet.

The server 501 can be adapted to store sequencing information, and/or information on a subject, such as, for example, polymorphisms, mutations, patient history of the subject, demographic data and/or other information of potential relevance. Such information can be stored on the storage unit 515 or the server 501 and such data can be transmitted through a network.

Methods as described herein can be implemented by way of machine (or computer processor) executable code (or software) stored on an electronic storage location of the server 501, such as, for example, on the memory 510, or electronic storage unit 515. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510. Alternatively, the code can be executed on a second computer system 540.

Aspects of the systems and methods provided herein, such as the server 501, can be embodied in programming Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" can refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

The computer readable medium can comprise computer executable code. The computer executable code can implement a method comprising: (a) accessing a data file in computer memory that comprises a plurality of sequencing reads corresponding to a first addressable location of a sequencing platform, wherein the sequencing reads are generating by subjecting a first nucleic acid template coupled to the addressable location to a first and at least a second round of sequencing, wherein the first and at least second rounds of sequencing are performed using a first and second sequencing primer, respectively; (b) using said data file, detecting a first detected allele at a first locus of the nucleic acid template and detecting a second detected allele at a second locus of the nucleic acid template; and (c) determining the first and second detected allele to be in phase based upon said detecting. The method executed by the computer executable code can further comprise the steps of (d) accessing a second data file in computer memory that comprises a plurality of sequencing reads corresponding to a second addressable location of a sequencing platform, wherein the sequencing reads are generating by subjecting a second nucleic acid template coupled to the addressable location to the first and the at least second round of sequencing; (e) using the second data file, detecting a first detected allele at a first locus of the second nucleic acid template and detecting a second detected allele at a second locus of the second nucleic acid template; and (f) determining the first and second detected alleles of the second nucleic acid template to be in phase with the first and second detected alleles of the first nucleic acid template if the first or second detected allele of the second nucleic acid template is shared in common with the first nucleic acid template.

Kits

Any of the compositions described herein may be comprised in a kit. In a non-limiting example, the kit, in a suitable container, comprises: an adaptor or several adaptors, one or more of oligonucleotide primers and reagents for ligation, primer extension and amplification. The kit may also comprise means for purification, such as a bead suspension, and nucleic acid modifying enzymes. Kits can further comprise instructions for practicing any of the phasing methods described herein.

Products

Products based on the methods provided herein may be commercialized by the Applicants under the Ovation® family. Ovation is a registered trademark of NuGEN Technologies, Inc.

The information gained from the phasing of alleles in a genome as provided by practicing the methods described herein can be of great utility in research and discovery as well as for clinical, diagnostic, forensic, archeological, geneological, and/or epidemiological applications. For example, haplotype information can be used to aid in the diagnosis, prognosis, and/or theranosis of a disease. For other example, haplotype information of a potential tissue or organ donor and organ recipient can aid in the assessment of HLA compatibilities of the donor and recipient for decreasing transplant rejection. In some cases, information gained from phasing of alleles in a genome of a subject can be used to tailor a healthcare or therapeutic regimen for the subject. In some cases, one or more methods described herein can be used to construct a database of haplotypes associated with one or more disease or biological trait. A haplotype obtained from a subject using a method as described herein can be compared against a haplotype database, thereby allowing for diagnosis and/or prognosis of a disease or condition. In some cases, haplotype information can be used to aid in the treatment of an infectious disease. For example, bacteria or virus infections can be associated with a plurality of drug resistant markers. Use of one or more phasing methods described herein can help determine if the plurality of drug resistant markers are due to co-infection with single-drug resistant strains or due to infection with a single strain that is multi-drug resistant. One or more phasing methods described herein can also be used to characterize T-cell receptor and/or immunoglobulin repertoire in a subject. For example, one or more phasing methods described herein can be used to assess V(D)J recombination in a subject. One or more phasing methods described herein can be used for diagnosing, predicting, determining or assessing the genetic characteristics of a fetus or embryo. A phasing method described herein can be used to assess genetic phasing within the genome of a developing fetus. In some cases, one or more phasing methods can be used to combat bioterrorism and/or to assess an epidemic or pandemic (e.g., by characterizing or identifying an infectious agent such as a virus or bacterium). In some cases, one or more phasing methods can be used for paternity testing, to establish a family tree, or to determine ancestry. In some cases, one or more phasing methods can be used to determine alternative splicing of RNA transcripts.

EXAMPLES

Figure 7:
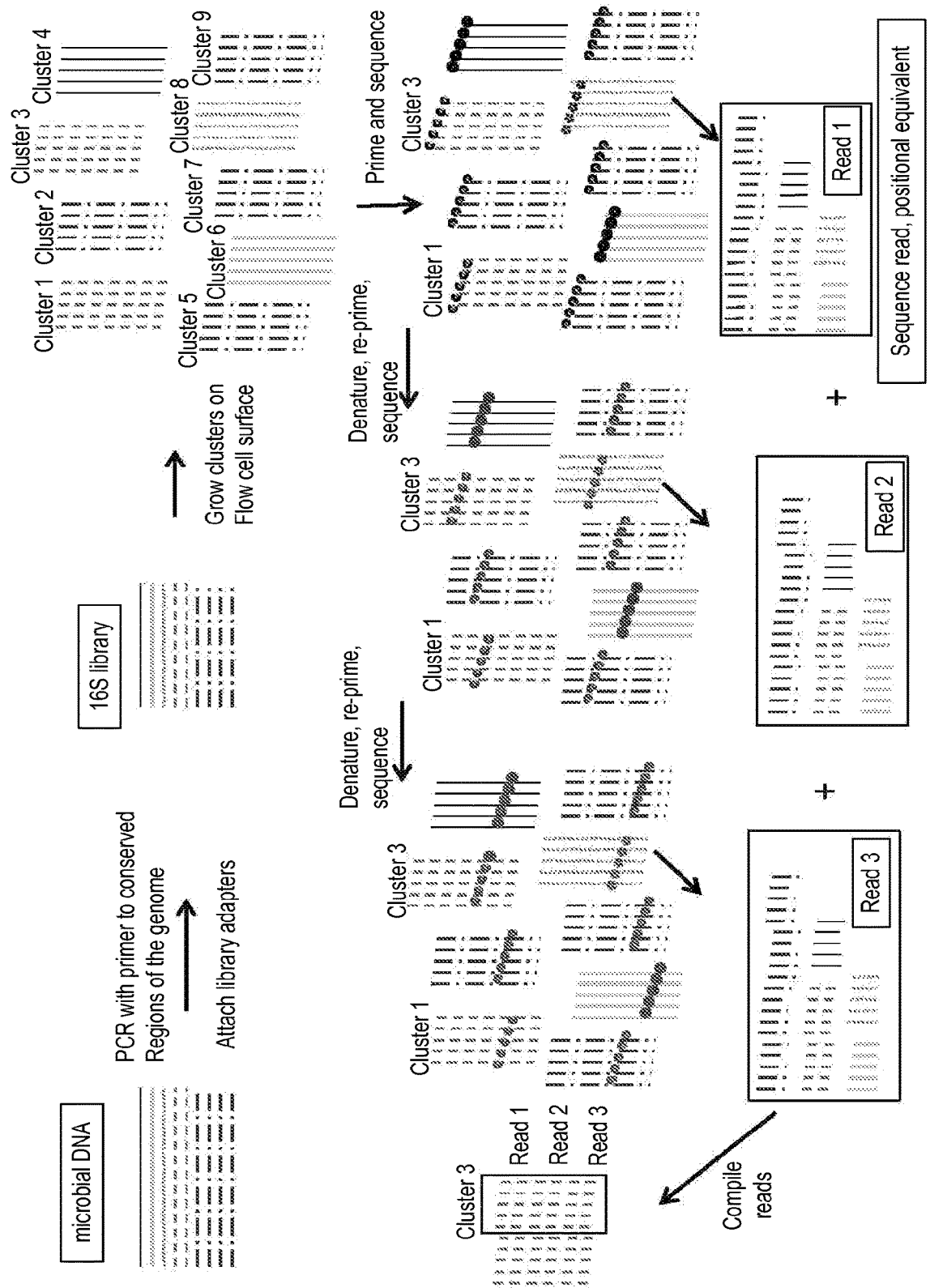
FIG. 7 depicts sequential sequencing method as applied to 16S microbial rRNA characterization, as described in Example 1.

Example 1—Characterization of the Human Oral Microbiome by Sequential Sequencing of Bacterial 16S Ribosomal Operon This example describes the characterization of the human oral microbiome by sequencing of the 16S rRNA gene sequences of a number of related bacterial organisms. 16S rRNA gene sequences contain species-specific hypervariable regions that can provide means for bacterial identification. An exemplary embodiment of 16S rRNA sequential sequencing, described below, is depicted in FIG. 7.
Sample Nucleic Acid Microbial genomic DNA is isolated from human saliva using the OMNIgene-DISCOVER sample collection kit (DNA Genotek) according to the manufacturer's instructions. The different line shadings and hash marks indicate different microbial genomes (microbial DNA). The relative numbers (e.g., 4 hatched lines vs 1 gray line) reflect the different ratios of the organisms in the saliva sample. Extracted DNA is then fragmented via sonication to an average length of 1000 bp and purified using Agencourt AMPure XP beads (Beckman Coulter Genomics). In some cases, extracted DNA is not subjected to fragmentation. For example, the microbial genetic DNA can be optionally enriched for target polynucleotides comprising the 16S genomic regions using primers to conserved 16S regions of the genome, thereby generating 16S amplicons.
Generation 16 S Libraries with Ligated Adapters The NuGEN Ovation Ultralow Library System (NuGEN Technologies) is used to attach library adaptors to the DNA fragments, thereby generating next generation sequencing libraries from 100 ng of the purified sample according to manufacturer's instructions. Ligation products with a minimum length of 200 bp in length are purified by selective binding to Agencourt AMPure XP beads.
Sequential Primer Sequencing Library members are clonally amplified by bridge amplification on an Illumina flowcell, thereby generating spatially separated clusters, wherein the clusters comprise identical copies of an original sequencing library member. In a first round of sequencing, all clusters, including those containing 16 S ribosomal DNA fragments, are sequenced by Illumina sequencing system using an Illumina standard forward primer. The standard forward primer can be designed to hybridize to a sequencing primer binding site of a library adaptor. Alternatively, a custom primer may be used. The custom primer can be designed to hybridize to a location upstream of and to sequence an informative locus. In such cases, clusters comprising a primer binding site for the first custom primer can be sequenced. The first round of sequencing can generate a first sequencing read ("Read 1"). Following the first sequencing read, the DNA is denatured to wash away the newly synthesized strand comprising Read 1. In cases where the first sequencing primer is a standard forward primer, Read 1 can contain sequence information for the forward end of the cluster templates. In cases where the first sequencing primer is a custom primer, Read 1 can comprise sequence information for the informative locus. A second round of sequencing can then be performed using a second sequencing primer. The second sequencing primer can be a custom primer that is designed to hybridize to a location upstream of and to sequence an informative locus. In cases where the first round of sequencing is performed using a custom primer that sequences an informative locus, the second sequencing primer is a designed to hybridize to a location upstream of and to sequence informative locus which is downstream of the first informative locus. The second round of sequencing can produce a second sequencing read "Read 2" in clusters comprising a primer binding site for the second sequencing primer. Read 2 can comprise sequence information for the informative locus sequenced by the second sequencing primer. Successive rounds of denaturation, re-priming and sequencing are optionally performed with primers that are designed to sequence additional informative loci. Sequence reads from successive priming and sequencing are compiled for each cluster and aligned to map reads originating from the same nucleic acid fragments.

Figure 8:
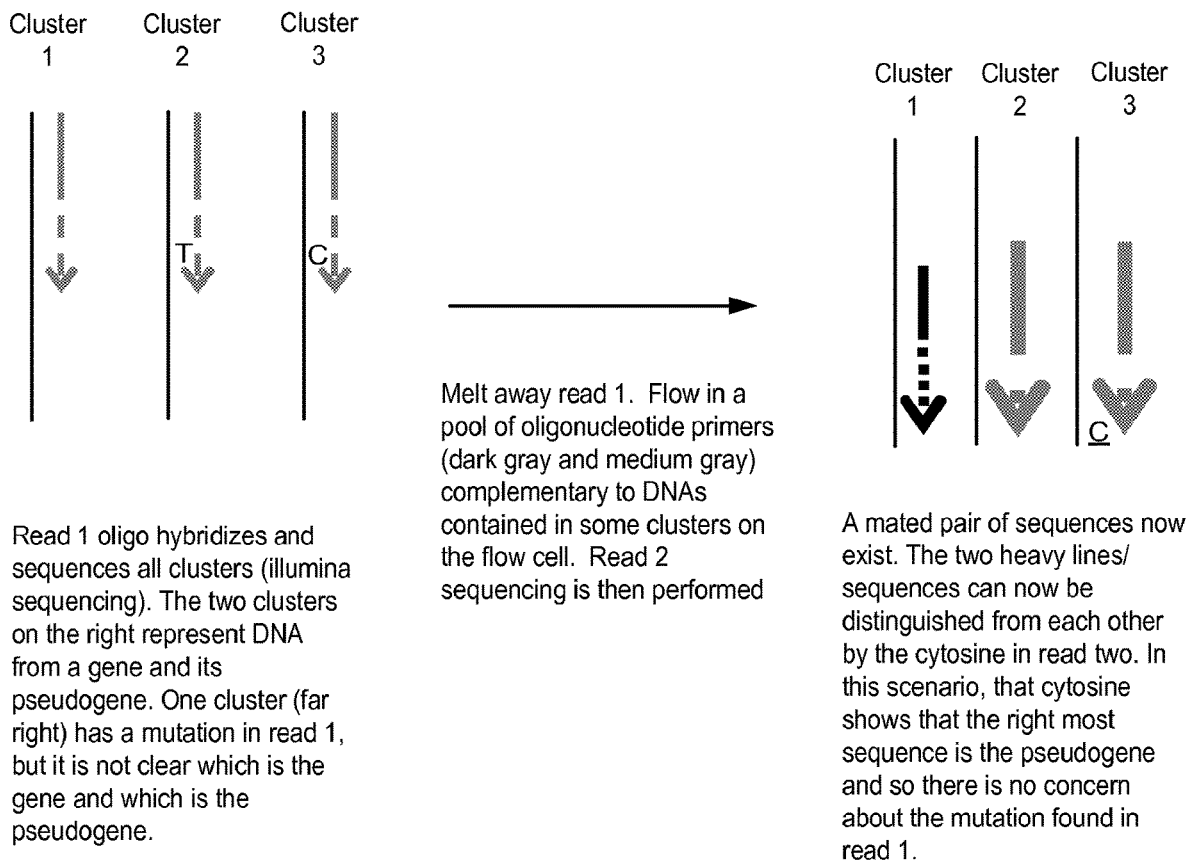
FIG. 8 depicts the use of specific oligonucleotide pools and the generation of mated pairs of sequencing reads to differentiate between two closely related nucleotide sequences, such as a gene/pseudogene pair.

Example 2—Genomic DNA Sequencing—Distinguishing Between a Gene and its Pseudogene Using Sequential Sequencing FIG. 8 depicts an exemplary application of a method described herein to distinguish a gene from a pseudogene in a gene/pseudogene pair. Genomic DNA sequencing libraries are prepared using the NuGEN's Encore system. These libraries are sequenced on a DNA sequencing system such as those made by Illumina or Ion Torrent. Clusters include, but are not limited to cluster 1, from a different genomic region from a gene/pseudogene pair, cluster 2, which comprises a portion of the gene of a gene/psuedogene pair, and cluster 3, which comprises a portion of the pseudogene of the gene/pseudogene pair. A first round of sequencing is performed using a first sequencing primer, thereby generating a first sequencing read. In some cases, the first sequencing primer is a standard forward primer as described in Example 1. The first sequencing read reveals that clusters 2 and 3 exhibit different alleles at a certain locus (a T in cluster 2 and a C in cluster 3). However, it is impossible to determine from read 1 which cluster represents the gene or the pseudogene. Following a first sequencing read, the DNA is denatured to wash away the extension strand. An oligonucleotide designed to anneal to a common sequence shared by the gene and pseudogene is injected into the sequencer to act as the second sequencing primer. The second sequencing primer can be designed to hybridize to a conserved sequence shared by the gene and pseudogene, wherein extension of the primer produces a second sequencing read that extends across a locus that can distinguish the gene and pseudogene. An exemplary gene/pseudogene pair which can be distinguished using a method described herein is the SMN1 gene/SMN2 pseudogene pair. In some embodiments, the second sequencing primer comprises a sequence which is designed to hybridize to a conserved sequence shared by SMN1 and SMN2, wherein extension of the primer produces a second sequencing read that extends across a locus that can distinguish SMN1 and SMN2. In one embodiment, the second sequencing primer comprises the sequence CTTCCTTTATTTTCCTTACAGGGT (SEQ. ID. NO: 1). The second sequencing read reveals a downstream C base call at the locus in cluster 3. The C base call reveals that cluster 3 maps to the pseudogene but that cluster 2 maps to the gene. An oligonucleotide set may include primers that will sequence through one of the nucleotide differences between the gene and pseudogene as well as primers that will generate sequence to read nucleotide differences, and therefore determine whether a sequencing read is from a gene or its pseudogene. A combination of such primers will allow multiple gene/pseudogene pairs across the genome to be analyzed simultaneously for genetic mutations.

Example 3—Targeted DNA Sequencing Library

A targeted DNA sequencing library is made using a target-selective library preparation kit from NuGEN, Agilent, Illumina, or Nimblegen, described herein. These libraries are sequenced on a DNA sequencing system such as those made by Illumina or Ion Torrent. Following a first sequencing read, the DNA is denatured to wash away the extension strand. A pool of primers that hybridize to common sequences in gene/pseudogene pairs are injected into the sequencer to act as a priming site for a second sequencing read. A primer set may include primers that will sequence through one of the nucleotide differences between a gene and its pseudogene (e.g., SMN1 and SMN2) as well as primers that will generate sequence to read nucleotide differences, and therefore determine whether a sequencing read is, for example, from a gene or pseudogene. A combination of such primers will allow multiple gene/pseudogene pairs across the genome to be analyzed simultaneously for genetic mutations. This type of technology is useful for genetic diagnostics.

Example 4—RNA-Sequencing Library

An RNA sequencing library is made from NuGEN's Encore Complete RNA-Seq Library System. The library is sequenced on an Illumina DNA sequencer. Following the first sequencing read, a pool of primers that will hybridize to specific exons of interest is injected into the sequencing machine. These primers are used to generate a second sequencing read in a downstream exon. The second, targeted sequencing read provides information about which exons have been spliced together to generate a particular RNA transcript.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments provided herein described herein may be employed in practicing the invention. It is intended that the following claims define the scope of the invention and that methods and structures within the scope of these claims and their equivalents be covered thereby.

What is claimed is:

1. A method, comprising:
   coupling a nucleic acid template strand to a solid support in a sequencing platform;
   sequencing the template strand using a first primer to produce a first sequencing read, the first primer comprising a 3' portion that anneals to a first binding site in the template strand;
   removing the first primer and an extension product from the template strand;
   annealing a second primer to a genomic location in the template strand that is more than 5 nucleotides away from a binding site of the first primer, wherein a 3' portion of the second primer is complementary to the genomic location in the template strand; and
   sequencing the template strand using the second primer to produce a second sequencing read, wherein at least one of the sequencing steps comprises sequencing by synthesis.

2. The method of claim 1, wherein the sequencing comprises sequencing by synthesis using a semiconductor chip.

3. The method of claim 2, wherein the semiconductor chip comprises an ion-sensitive field effect transistor and a micromachined well.

4. The method of claim 2, wherein the at least one step of sequencing by synthesis comprises sensing protons.

5. The method of claim 1, wherein the second binding site is more than 150 nt away from the first binding site.

6. The method of claim 2, wherein the coupling comprises conjugating the template strand to the solid support of the sequencing platform.

7. The method of claim 6, wherein the solid support comprises a bead.

8. The method of claim 1, wherein an adaptor oligonucleotide is ligated to one or both ends of the template strand.

9. The method of claim 8, wherein the first binding site is within the adaptor oligonucleotide.

10. The method of claim 9, wherein the second sequencing primer is not complementary to the adaptor oligonucleotide.

11. The method of claim 1, wherein the second sequencing read comprise an informative locus.

12. The method of claim 11, wherein the informative locus is a polymorphic locus.

13. The method of claim 1, wherein the first sequencing read comprises a first informative locus and wherein the second sequencing read comprises a second informative locus.

14. The method of claim 13, comprising determining that a first allele detected at the first informative locus and a second allele detected at the second informative locus are in phase.

15. The method of claim 14, wherein the first allele and the second allele are separated by a distance of over 150 bases.

16. The method of claim 1, further comprising subjecting the template strand to an additional round of sequencing by:
   removing a previously annealed primer from the template strand;
   annealing an additional primer to a second genomic location in the template strand; and
   sequencing the template strand from the additional primer, thereby producing an additional sequencing read.

17. The method of claim 16, wherein a first allele detected by the first sequencing read, a second allele detected by the second sequencing read, and an additional allele detected by the additional sequencing read are determined to be in phase.

* * * * *

SEQUENCE LISTING

```
<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: Synthetic primer

<400> SEQUENCE: 1
cttcctttat tttccttaca gggt                                     24
```